(12) United States Patent
Adams et al.

(10) Patent No.: US 8,246,581 B2
(45) Date of Patent: *Aug. 21, 2012

(54) DISPOSABLE INFUSION DEVICE WITH REDUNDANT VALVED SAFETY

(75) Inventors: John M. Adams, Snohomish, WA (US); Brett J. Carter, Monroe, WA (US)

(73) Assignee: Calibra Medical, Inc., Redwood City, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 13/150,395

(22) Filed: Jun. 1, 2011

(65) Prior Publication Data

US 2011/0230838 A1 Sep. 22, 2011

Related U.S. Application Data

(62) Division of application No. 12/147,283, filed on Jun. 26, 2008, now Pat. No. 7,976,500.

(51) Int. Cl.
*A61M 1/00* (2006.01)
(52) U.S. Cl. ....................................... 604/151
(58) Field of Classification Search .................. 604/151
See application file for complete search history.

(56) References Cited

U.S. PATENT DOCUMENTS

| 4,360,019 | A | * | 11/1982 | Portner et al. ................. 604/131 |
| 5,056,992 | A | | 10/1991 | Simons et al. |
| 6,270,481 | B1 | | 8/2001 | Mason et al. |
| 2002/0177809 | A1 | | 11/2002 | Kriesel et al. |
| 2003/0229310 | A1 | | 12/2003 | Flaherty et al. |
| 2009/0088682 | A1 | | 4/2009 | Cross et al. |
| 2009/0088689 | A1 | | 4/2009 | Carter |
| 2009/0088693 | A1 | | 4/2009 | Carter |
| 2009/0088694 | A1 | | 4/2009 | Carter et al. |

OTHER PUBLICATIONS

International Search Report for International Application No. PCT/US2009/048926, dated Jan. 25, 2010.

* cited by examiner

*Primary Examiner* — Nicholas Lucchesi
*Assistant Examiner* — Jason Flick
(74) *Attorney, Agent, or Firm* — Richard O. Gray, Jr.; Graybeal Jackson LLP

(57) ABSTRACT

A wearable infusion device comprises a reservoir that holds a liquid medicament, an outlet port that delivers the liquid medicament to a patient, a pump that holds a volume of the liquid medicament received from the reservoir and displaces substantially all of the volume of the liquid medicament when actuated, and at least a first valve, a second valve, and a third valve. The valves establish fluid connection between the reservoir and the pump when in a first valve configuration and establish fluid connection between the pump and the outlet when in a second valve configuration. At least two of the valves isolate the outlet from the reservoir when the valves are in the first valve configuration.

2 Claims, 15 Drawing Sheets

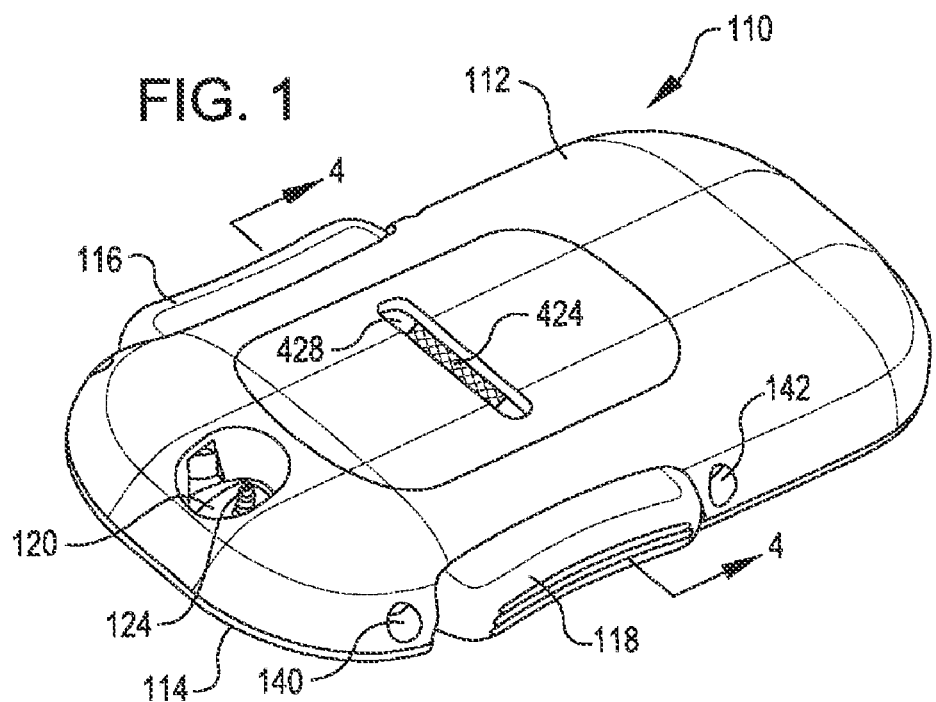
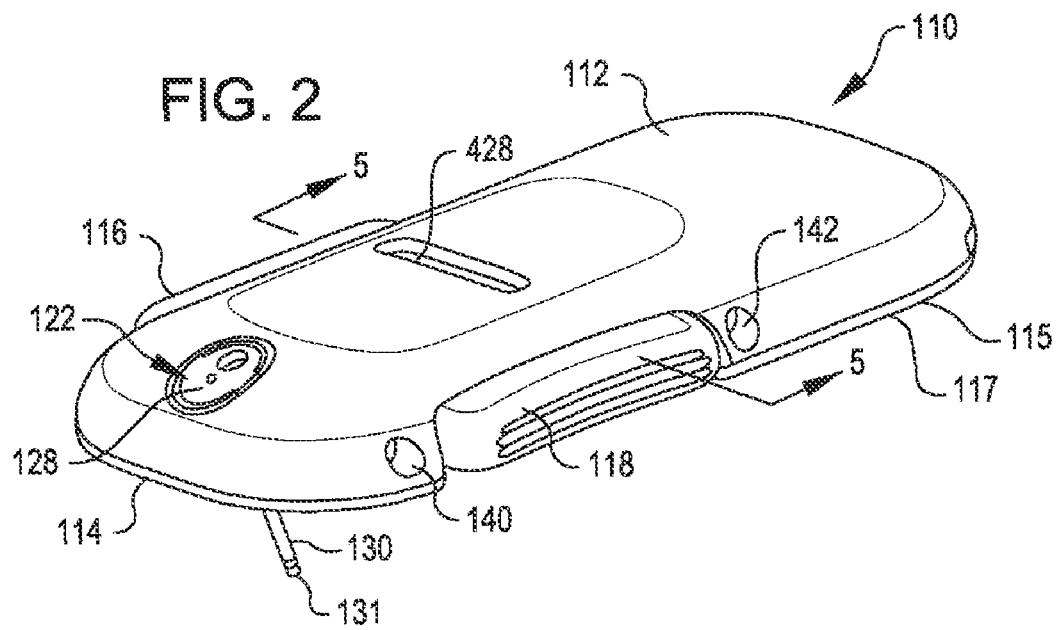

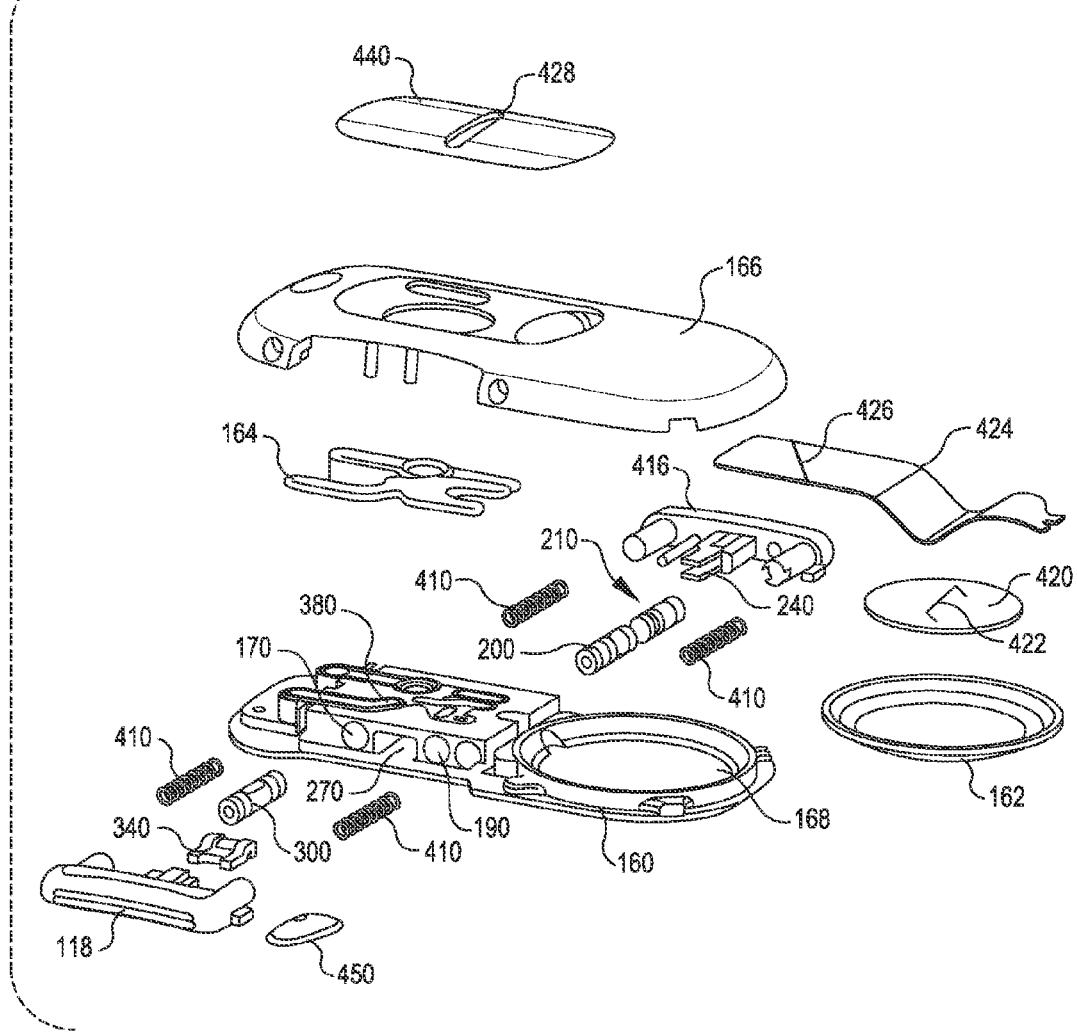

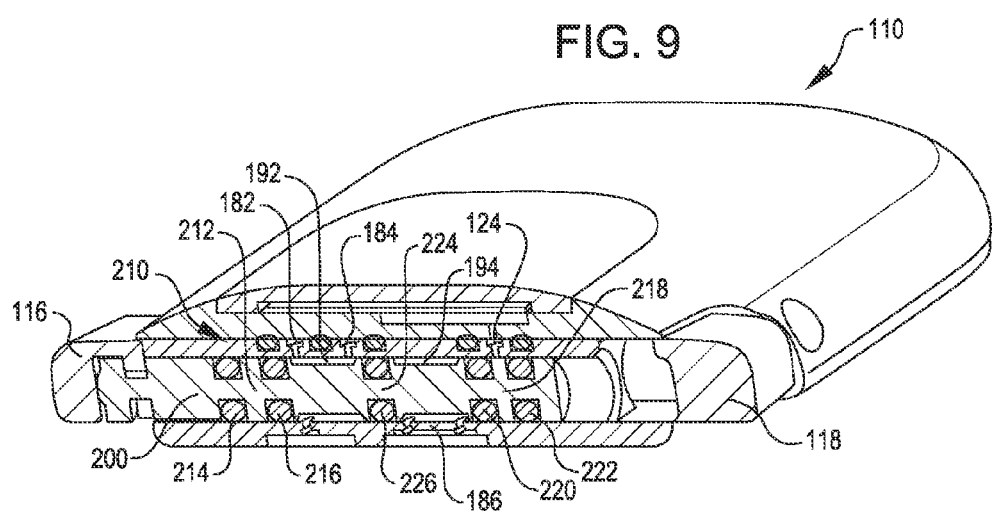
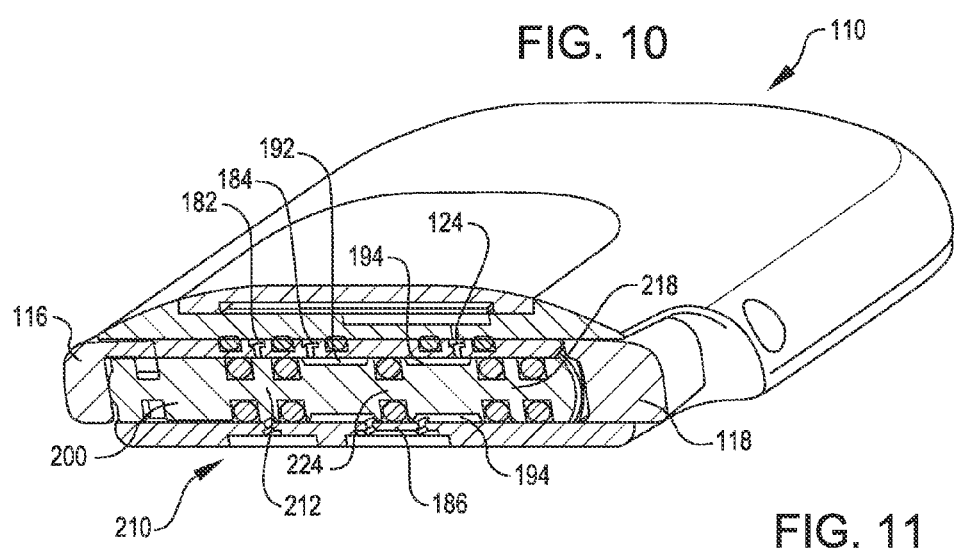
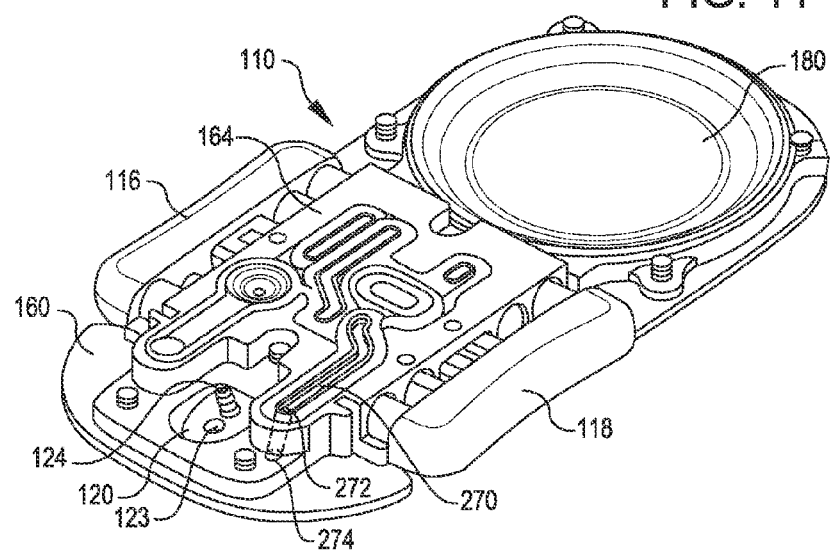

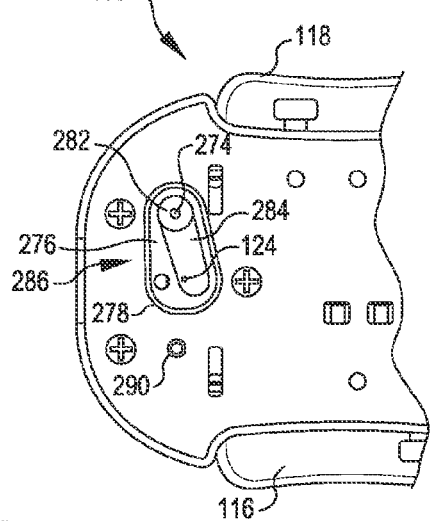
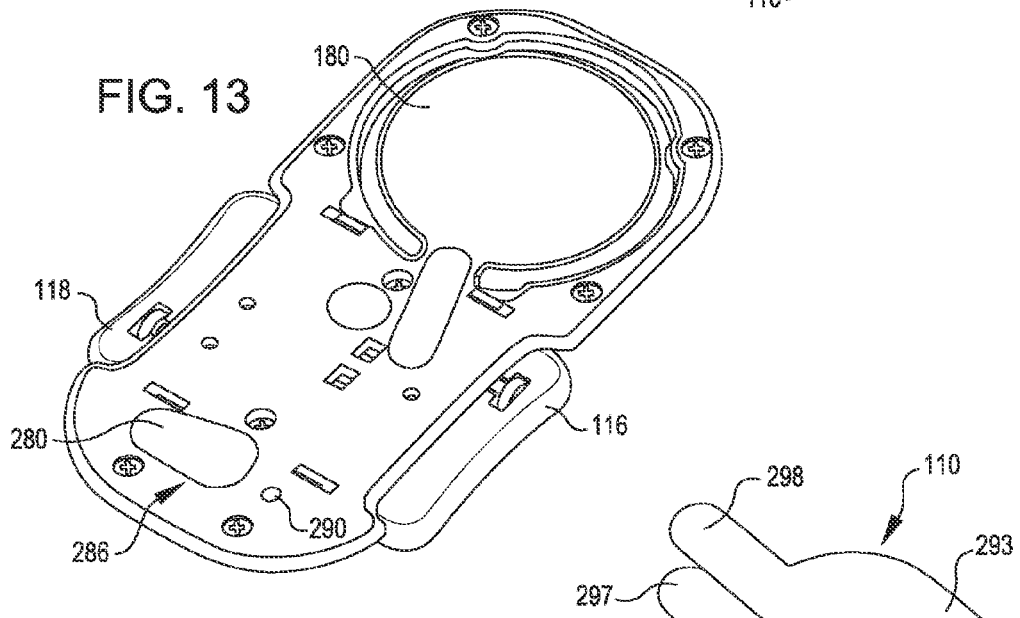
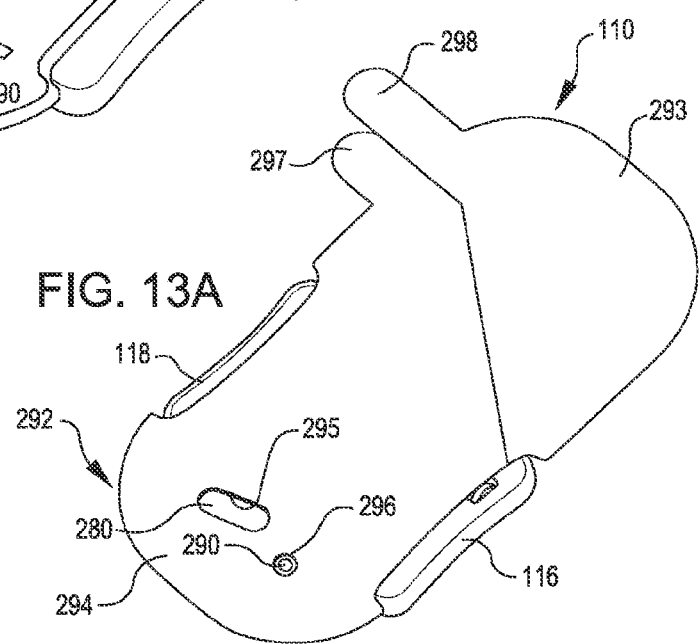

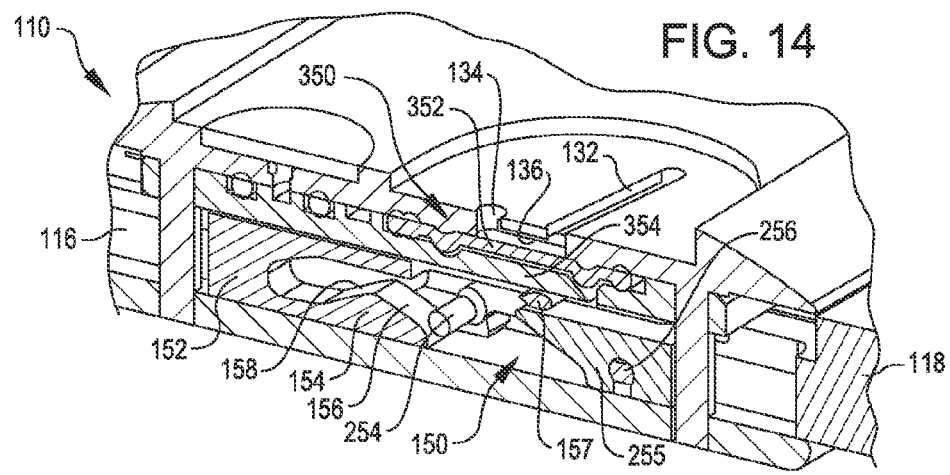
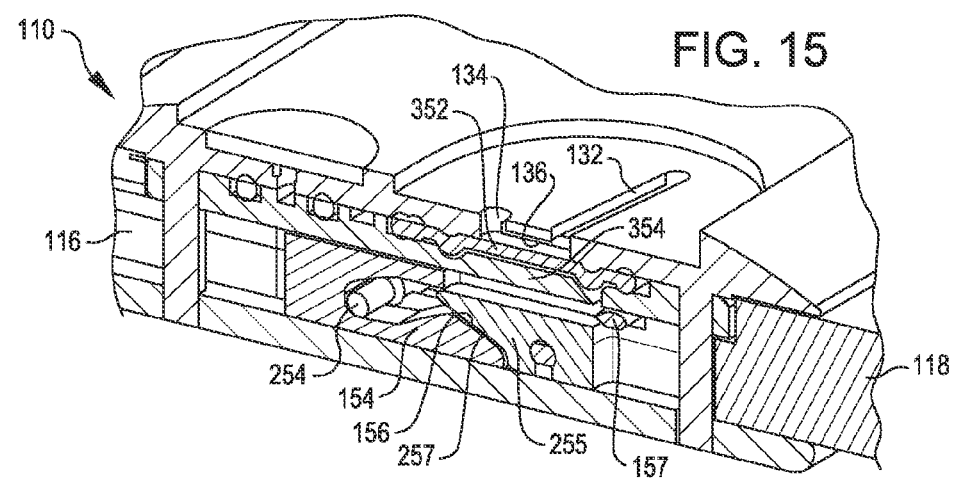
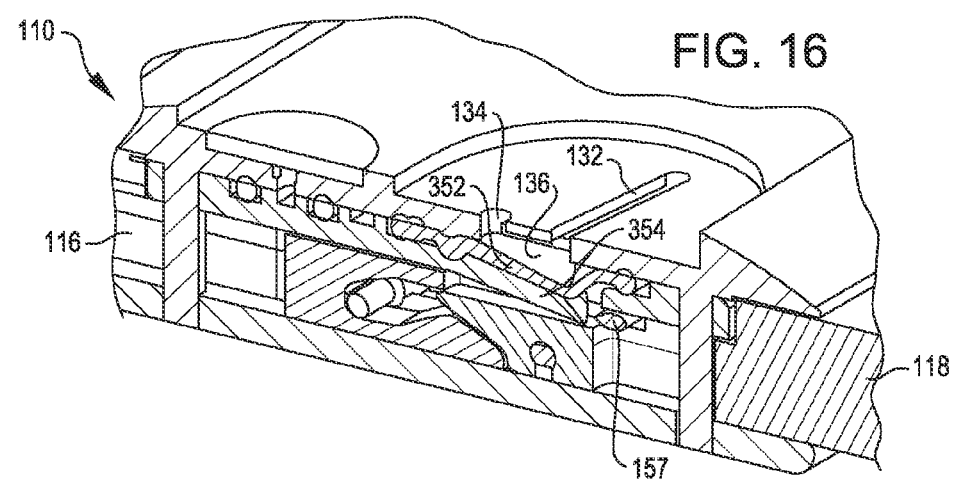

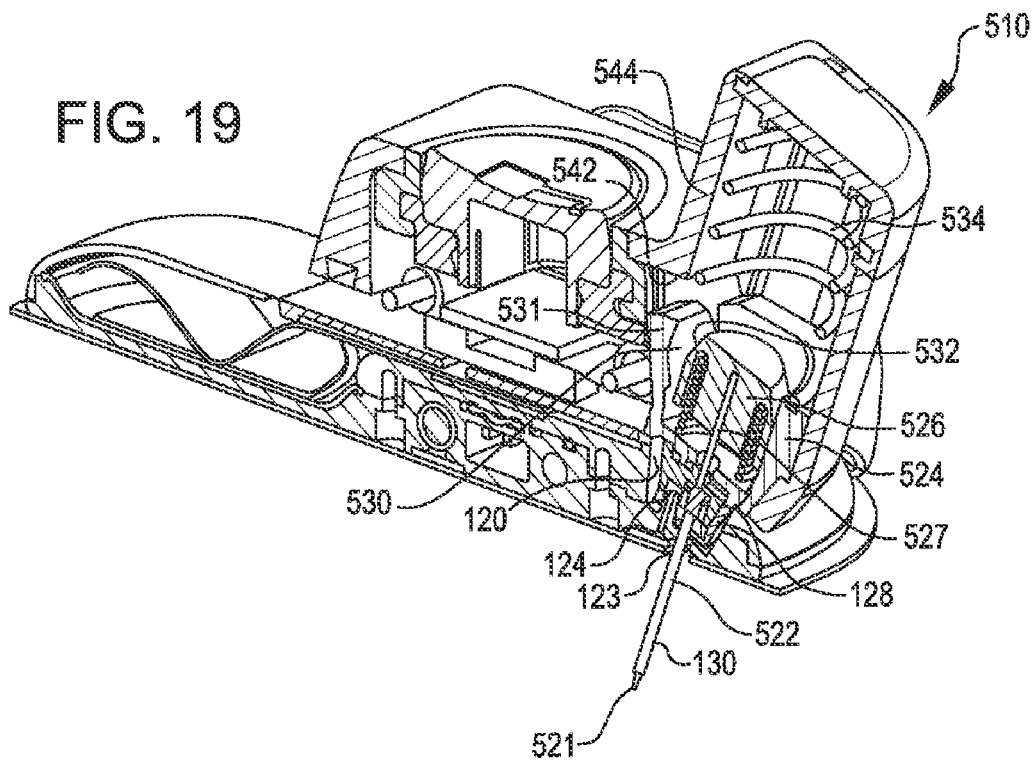
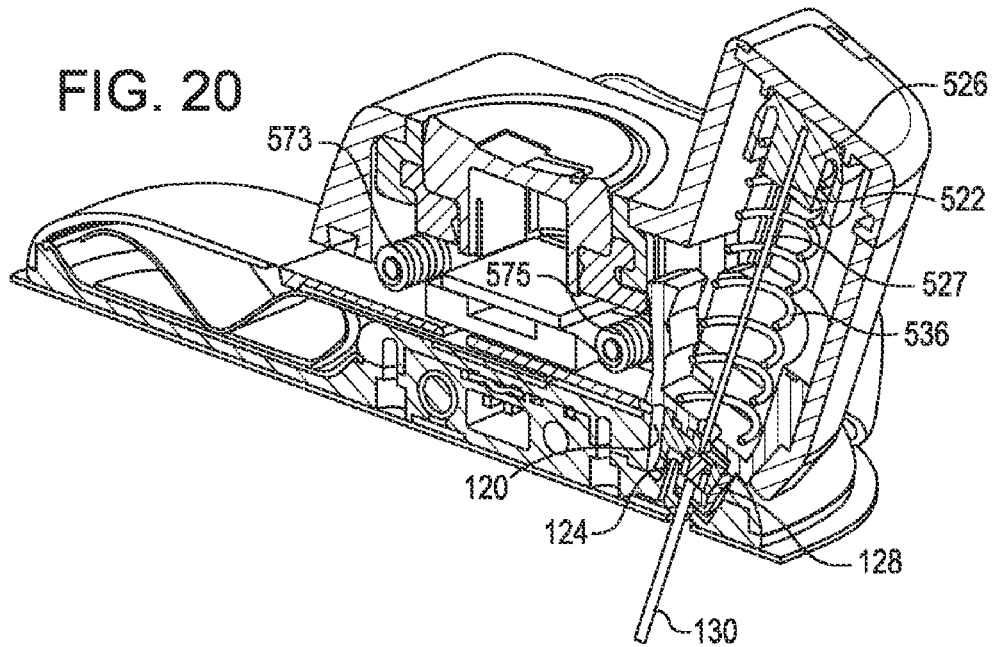

DISPOSABLE INFUSION DEVICE WITH REDUNDANT VALVED SAFETY

The present application is a divisional of co-pending U.S. patent application Ser. No. 12/147,283, filed Jun. 26, 2008, which application is incorporated by reference herein in its entirety.

BACKGROUND OF THE INVENTION

The present invention relates to infusion devices and more particularly to such devices that enable liquid medicaments to be conveniently and safely self-administered by a patient.

Administration of insulin has traditionally been accomplished using a syringe. Recently, needle carrying pen-like devices have also been employed for this purpose. Both forms of insulin administration require the patients to stick themselves each time they inject insulin, often many times a day. Thus, these traditional forms of insulin administration have been a rather pervasive intrusion in the lives and routines of the patient's who have had to adopt and employ them.

More recently, insulin pumps attached by tubing to an infusion set mounted on the patient's skin have been developed as an alternative form of insulin administration. Such pumps may be controlled by a programmable remote electronic system employing short range radio communication between a control device and electronics that control the pump. While such devices may involve fewer needle sticks, they are expensive to manufacture. They are also complex to operate and cumbersome and awkward to wear. Further, the cost of such devices can be many times the daily expense of using a traditional injection means such as a syringe or an insulin pen.

Devices of the type mentioned above also require a significant amount of training to control and thus use the devices. Great care in programming the devices is required because the pumps generally carry sufficient insulin to last a few days. Improper programming or general operation of the pumps can result in delivery of an excessive amount insulin which can be very dangerous and even fatal.

Many patients are also reluctant to wear a pump device because they can be socially awkward. The devices are generally quite noticeable and can be as large as a pager. Adding to their awkwardness is their attachment to the outside of the patients clothes and the need for a catheter like tubing set running from the device to an infusion set located on the patient's body. Besides being obvious and perhaps embarrassing, wearing such a device can also be a serious impediment to many activities such as swimming, bathing, athletic activities, and many activities such as sun bathing where portions of the patient's body are necessarily uncovered.

In view of the above, a more cost effective and simple device has been proposed whereby an injection system is discreetly attached directly to the skin of the patient. The device may be attached to the patient under the patient's clothing to deliver insulin into the patient by the manual pumping of small doses of insulin out the distal end of a temporarily indwelling cannula that is made a part of the pump device. The cannula may be made a part of the drug delivery device before, during or after the attachment of the drug delivery device to the skin of the patient. The device may be made quite small and, when worn under the clothes, entirely unnoticeable in most social situations. It may still carry sufficient insulin to last a patient several days. It can be colored to blend naturally with the patient's skin color so as not to be noticeable when the patient's skin is exposed. As a result, insulin for several days may be carried by the patient discreetly, and conveniently applied in small dosages after only a single needle stick. For a more complete description of devices of this type, reference may be had to co-pending application Ser. No. 11/906,130, filed on Sep. 28, 2007 for DISPOSABLE INFUSION DEVICE WITH DUAL VALVE SYSTEM, which application is owned by the assignee of this application and hereby incorporated herein by reference in its entirety.

The present invention provides further improvement to the devices disclosed in the above referenced co-pending application. More particularly, the devices disclosed herein provide for improved patient safety and/or convenience. For example, embodiments of the invention provide, for example, improved sealing of the medicament, more convenient cannula deployment, device misuse prevention, primed and dosage ready indication and fluid path occlusion detection. These and other advantages are addressed herein.

SUMMARY OF THE INVENTION

In one embodiment, a wearable infusion device comprises a reservoir that holds a liquid medicament, an outlet port that delivers the liquid medicament to a patient, a pump that displaces a volume of the liquid medicament when actuated, and at least a first valve, a second valve, and a third valve, the valves establishing fluid connection between the reservoir and the pump when in a first valve configuration and establishing fluid connection between the pump and the outlet when in a second valve configuration. At least two of the valves isolate the outlet from the reservoir when the valves are in the first valve configuration.

The valves are arranged to prevent the outlet from being in fluid connection with the reservoir. The device my further include a first control that sets the configuration of the valves and a second control that actuates the pump.

The device may further comprise a linkage that precludes the second control from actuating the pump until the first control sets the valves into the second valve configuration. The valves may be arranged to prevent the outlet from being in fluid connection with the reservoir.

The first, second, and third valves may comprise a shuttle valve. The valves may be arranged to prevent the outlet from being in fluid connection with the reservoir.

The device may further comprise a first control that sets the configuration of the valves and a second control that actuates the pump. A linkage may preclude the second control from actuating the pump until the first control sets the valves into the second valve configuration.

The valves may be operable independently from the pump. The valves and the pump may be operable solely by manual force applied to the first and second control. The pump may be a piston pump.

In another embodiment, a wearable infusion device comprises a reservoir that holds a liquid medicament, an outlet port that delivers the liquid medicament to a patient, and a pump that holds a volume of the liquid medicament received from the reservoir and displaces substantially all of the volume of the liquid medicament when actuated. A shuttle valve comprising a first valve, a second valve, and a third valve establishes fluid connection between the reservoir and the pump when in a first valve configuration and fluid connection between the pump and the outlet when in a second valve configuration. At least two of the valves isolate the outlet from the reservoir when the valves are in the first valve configuration.

The valves are arranged to prevent the outlet from being in direct fluid connection with the reservoir. A first control sets the configuration of the valves and a second control actuates the pump.

The device may further comprise a linkage that precludes the second control from actuating the pump until the first control sets the valves into the second valve configuration. The valves are arranged to prevent the outlet from being in fluid connection with the reservoir.

The valves are operable independently from the pump.

The valves and the pump may be operable solely by manual force applied to the first and second control. The pump may be a piston pump.

In a still further embodiment, a wearable infusion device comprises a reservoir that holds a liquid medicament, an outlet port that delivers the liquid medicament to a patient, and a fluid pathway between the reservoir and the outlet. The device further comprises a pump that pumps the liquid medicament between the reservoir and the outlet when actuated, and at least a first valve, a second valve, and a third valve. The valves form a first valve configuration and a second valve configuration and are movable between the first configuration and the second configuration such that when the valves are in the first configuration, the fluid pathway between the reservoir and the pump is open and the fluid pathway between the pump and the outlet is closed, and when the valves are in the second configuration, the fluid pathway between the reservoir and the pump is closed and the fluid pathway between the pump and the outlet is open. At least two of the valves isolate the outlet from the reservoir.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 1 is a perspective view of an infusion device embodying the present invention shown without a deployed cannula;

FIG. 2 is another perspective view of the infusion device of FIG. 1 shown with a deployed cannula;

FIG. 3 is an exploded perspective view of the device of FIG. 1;

FIG. 9 is a sectional view, in perspective, to an enlarged scale, showing the configuration of the valves of the device of FIG. 1 during pump filling and prior to medicament dosage delivery;

FIG. 10 is another sectional view, in perspective, to an enlarged scale, showing the configuration of the valves of the device of FIG. 1 during dosage delivery;

FIG. 11 is a top perspective view of the base of the device of FIG. 1 illustrating various fluid paths within the device;

FIG. 12 is a partial bottom plan view of the base of the device of FIG. 1 to illustrate the interior of a prime indicator according to one embodiment thereof;

FIG. 13 is a bottom plan view of the base of the device of FIG. 1 illustrating the prime indicator interior covered by a translucent cover according to the above mentioned prime indicator embodiment;

FIG. 13A is a bottom view of the device 110 illustrating a removable non-adhesive layer overlying an adhesive layer on the device base;

FIG. 14 is a sectional view in perspective of an occlusion detector and lock-out according to an embodiment of the device of FIG. 1 shown prior to an intended dosage delivery;

FIG. 15 is another sectional view in perspective of the occlusion detector and lock-out shown during an intended dosage delivery;

FIG. 16 is another sectional view in perspective of the occlusion detector and lock-out shown during occlusion detection and just prior to lock-out;

FIG. 19 is a sectional view like that of FIG. 18, showing the device and cannula placement assembly during cannula deployment;

FIG. 20 is a sectional view like that of FIG. 18, showing the device and cannula placement assembly after cannula deployment;

DETAILED DESCRIPTION OF THE INVENTION

Figure 4:
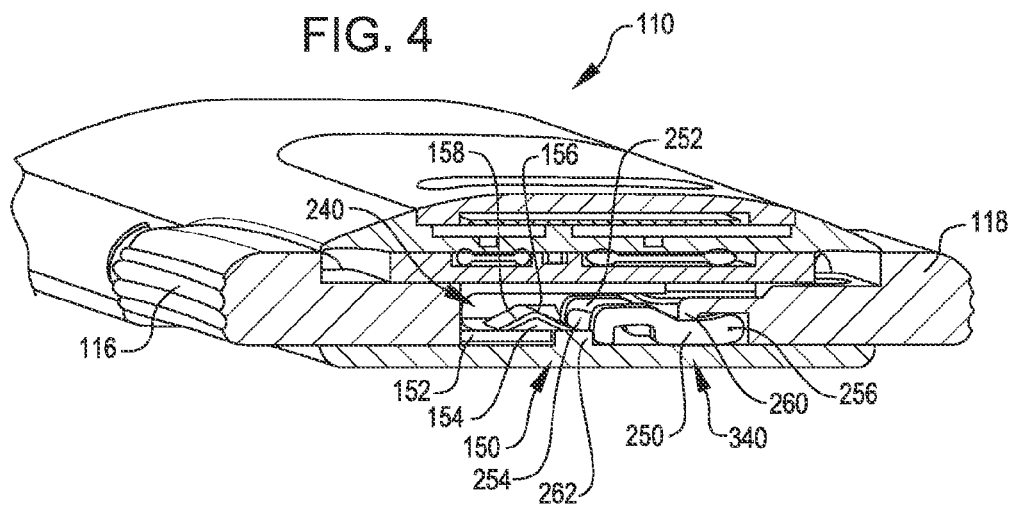
FIG. 4 is a sectional view, in perspective, to an enlarged scale, taken along lines 4-4 of FIG. 1, showing the actuation linkages of the device of FIG. 1 prior to medicament dosage delivery.

Referring now to FIGS. 1 and 2, they are perspective views of an infusion device 110 embodying various aspects of the present invention. FIG. 1 shows the device prior to receiving and thus without a cannula while FIG. 2 illustrates the device after having received a cannula 130 that has a distal end 131. As may be seen in both FIGS. 1 and 2, the device 110 generally includes an enclosure 112, a base 114, a first actuator control button 116, and a second actuator control button 118.

The enclosure 112, as will be seen subsequently, is formed by virtue of multiple device layers being brought together. Each layer defines various components of the device such as, for example, a reservoir, fluid conduits, pump chambers, and valve chambers, for example. This form of device construction results in a compact design and enables manufacturing economy to an extent that the device is disposable after use.

The base 114 preferably includes a pad 115 attached to the base 114. The pad 115 has an adhesive coating 117 on the side thereof opposite the base 114 to permit the device to be adhered to a patient's skin. The adhesive coating may originally be covered with a releasable cover 292 (FIG. 13A) that may be pealed off of the adhesive layer 117 when the patient endeavors to adhere the device 110 to their skin.

The device 110, as will be seen herein after is first adhered to the patient's skin followed by the deployment of the cannula 130 thereafter. However, it is contemplated herein that various aspects of the present invention may be realized within a device that may alternatively be mated with a previously deployed cannula assembly.

The actuator buttons 116 and 118 are placed on opposites sides of the device 110 and directly across from each other. This renders more convenient the concurrent depression of the buttons when the patient wishes to receive a dose of the liquid medicament contained within the device 110. This arrangement also imposes substantially equal and opposite forces on the device during dosage delivery to prevent the device from being displaced and possibly stripped from the patient. As will be further seen hereinafter, the concurrent depression of the buttons is used to particular advantage. More specifically, the actuator button 116 may serve as a valve control which, when in a first position as shown, establishes a first fluid path between the device reservoir and the device pump to support pump filling, and then, when in a second or depressed position, establishes a second fluid path between the device pump and the device outlet or distal end of the cannula to permit dosage delivery to the patient. As will be further seen, a linkage between the control actuator buttons 116 and 118 permits actuation of the device pump with the actuator control button 118 only when the second fluid path has been established by the first actuator control button 116. Hence, the first actuator control button 116 may be considered a safety control.

The actuator buttons 116 and 118 are preferably arranged to require a complete through of their travel to achieve activation of the device pump and thus dosage delivery. This, together with the sudden release of resistance to actuator advancement creates a snap action that provides an advantage in positively knowing that dosage delivery has occurred and that no less than a full dose has been delivered. For more description regarding this feature, reference may be had to co-pending application Ser. No. 11/906,102, titled DISPOSABLE INFUSION DEVICE WITH SNAP ACTION ACTUATION, which application is owned by the assignee of this application and is incorporated herein by reference in its entirety.

As may be noted in FIG. 1, the device 110 includes a cavity 120 that is arranged to receive a cannula assembly 122 (FIG. 2) from which the cannula 130 extends. When the cannula is deployed, the outlet 124 of the device 110 is placed in fluid communication with the cannula 130 by a cannula carrier 128 of the cannula assembly 122 that carries the cannula. When thus deployed, the cannula 130 extends from the base 114 of the device 110 to beneath the skin of the user.

As may further be noted in FIGS. 1 and 2, the enclosure 112 of the device 110 includes a pair of pockets 140 and 142 on opposite sides of the second actuator button 118. A similar pair of pockets, not seen in the figure, are also provided on opposite sides of the first actuator button 116. These pockets are used to receive corresponding projections of a cannula placement assembly for releasably joining the cannula placement assembly to the device 110 to support cannula deployment as will be described subsequently. As will also be seen, upon cannula deployment, the cannula placement assembly is automatically released from the device by the driver projections being forced from the pockets.

Referring now to FIG. 3, it is an exploded perspective view of the device 110 of FIG. 1. It shows the various component parts of the device. The main component parts include the aforementioned device layers including the base layer 160, a reservoir membrane 162, an intermediate layer 164 and a top body layer 166. As may also be seen in FIG. 3, the base layer 160 is a substantially rigid unitary structure that defines a first reservoir portion 168, a pump chamber 170, and a valve chamber 190 that receives a shuttle bar 200 of a shuttle valve 210. A reservoir membrane layer 162 is received over the reservoir portion 168 to form an expandable/deflatable reservoir of the device 110. The base layer 160 may be formed of plastic, for example. The base and the top body layer may be joined together, trapping the intermediate layer there between by any means such as with screws, ultrasonic welding or laser welding.

The valve chamber 190 is arranged to receive a valve shuttle bar 200 carried by and extending from the first actuator button 116. A series of O-rings, to be described subsequently, are seated on the shuttle bar 200 to form first, second, and third valves. The actuator button 116 also carries a first linkage portion 240 of the linkage that permits actuation of the device pump with the actuator control button 118 only when the second fluid path has been established by the first actuator control button 116. The first linkage portion 240 is received within a suitably configured bore 270 formed in the base layer 160 and will be described subsequently.

The pump actuator button 118 is arranged to be linked to a pump piston 300 and a second linkage portion 340 to interact with the first linkage portion 240. The pump piston 300 is arranged to be received within the pump chamber 170 and the second linkage portion 340 is arranged to be received within the bore 270 for interacting with the first linkage portion 240. O-rings are seated on the piston 300 to provide a seal against leakage and to prevent external contaminants from entering the piston chamber.

The intermediate layer 164 may be a generally resilient member and received on the base layer 160 to cover channels scribed in the base layer as a type of gasket to form fluid channels 380 that serve to conduct the medicament from the reservoir to the device outlet and to the distal end 131 (FIG. 2) of the cannula 130. Springs 410 are arranged to spring load the actuator buttons 116 and 118 away from each other.

The reservoir membrane 162 is formed of flexible membrane material and is received over the reservoir portion 168 to form the reservoir of the device 110. A rigid plate 420 is arranged to be adhered to the reservoir membrane 162 of the reservoir. Because the membrane 162 is flexible, it will move as the reservoir is filled and emptied. The rigid plate 420 will then move with it. The plate 420 includes an eyelet 422 dimensioned to receive an elongated web 424 that forms a part of a medicament level indicator. The web 424 carries an indicator line or feature 426 that may be read through a window 428 of the device top most panel 440.

Another component of the device 110 is a translucent window 450 that is received on the underside of the base 160. As will be seen hereinafter, the window forms a part of a prime indicator. It is formed of a transparent material such as glass or transparent plastic and has a roughened surface rendering it translucent. However, when it is covered with or at least wetted by liquid medicament, it is rendered essentially transparent creating a visually obvious condition and, for example, permitting indicia to be seen beneath it indicating that the conduit to the device outlet is primed and ready to deliver fixed doses of medicament when desired.

Figure 5:
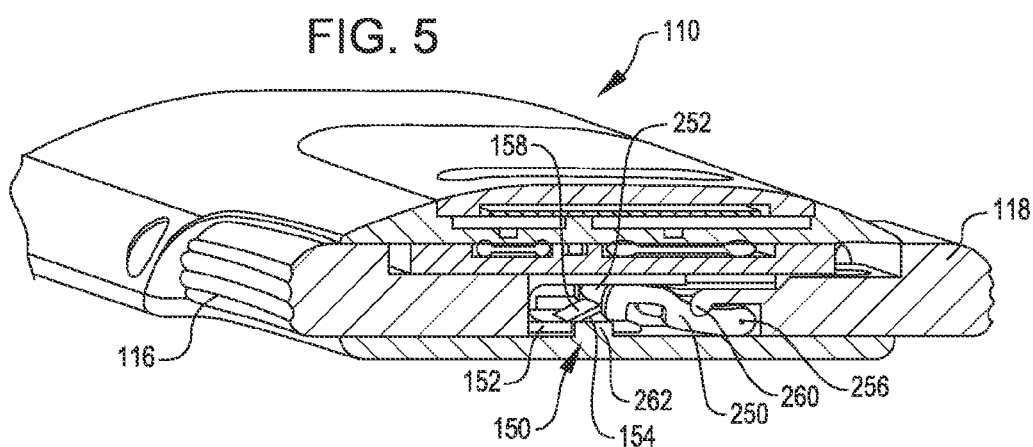
FIG. 5 is another sectional view, in perspective, to an enlarged scale, taken along lines 5-5 of FIG. 2, showing the actuation linkage operation of the device of FIG. 1 during medicament dosage delivery.
Figure 6:
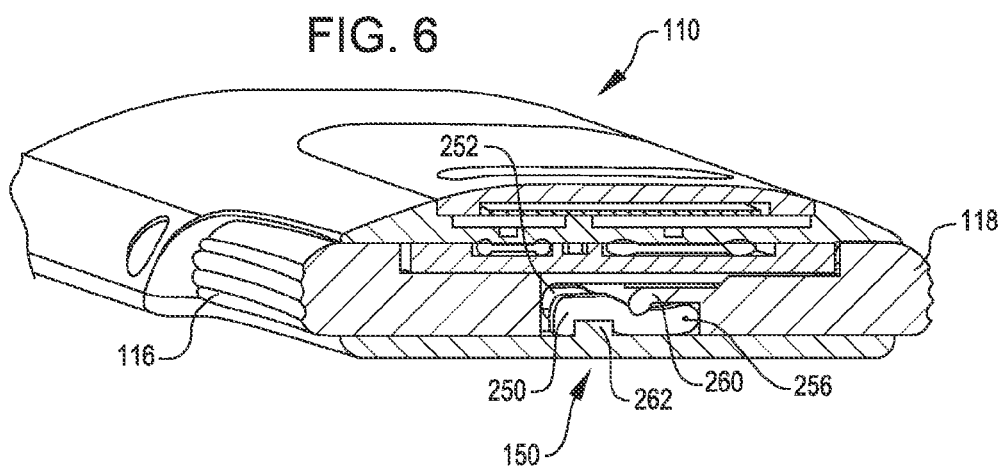
FIG. 6 is another sectional view similar to that of FIG. 5, in perspective, to an enlarged scale, showing the actuation linkage operation of the device of FIG. 1 immediately after dosage delivery.

FIGS. 4-6 show details of the operation of the linkage that permits actuation of the device pump with the actuator control button 118 only when the second fluid path from the reservoir to the outlet has been established by the first actuator control button 116. The linkage has been given the general reference character 150.

As may be seen FIG. 4, the first actuator button 116 has an extension 152 that terminates in a block 154. The block 154 has a first ramp surface 156 and a second ramp surface 158. When the device 110 is actuated, the button 116 is concurrently depressed with pump button 118. It and its extension 152 and block 154 are free to move to the right. As seen in FIGS. 4 and 5, the pump actuator button 118 has parallel extensions 250 and 252 which are joined and separated be a rod member 254. The extensions 250 and 252 are pivotally mounted to pivot about a pivot point 256. Another extension 260 of the pump actuator button 118 spring biases the extensions 250 and 252 as shown in FIG. 4. As seen in FIG. 4, the extensions 250 and 252 abut an abutment 262 which they must clear to enable the actuator 118 to be moved to the left. As shown in FIG. 5, as the button 116 is depressed, its extension 152 moves to the right causing the first ramp surface 156 to engage the rod member 254. Continued movement of the button causes the rod member 254 to ride up the first ramp surface 156 which in turn causes the extensions 250 and 252 to begin to move slightly to the left and bend upward against the loading of extension 260. Eventually, the rod member 254 rides up the length of the first ramp 156 and down the second ramp 158 causing the extensions 250 and 252 to clear the abutment 262 and continue their travel to the left until the extensions are received on the opposite side of the abutment as shown in FIG. 6. The pump button 116 has now been fully depressed to deliver a dose of measured medicament. When the ends of extensions 250 and 252 totally clear the abutment 262, they will snap behind the abutment 262 as shown in FIG. 6 and become temporarily locked. Meanwhile, the rod member 254 has traversed all the way down the second ramp surface 158. The buttons 116 and 118 are now fully depressed.

Hence, from the above, it may be seen that the pump button 118 could not at first move freely while the first actuator button 116 which operates the valves could. As a result, the pump actuation lags behind the valve actuation. This enables the device outlet to be sealed from the reservoir and the pump connected to the outlet before the pump is permitted to pump any medicament to the outlet. Hence, the device establishes a medicament delivery flow path to the cannula before the pump is able to begin pumping the medicament to the patient. Thus, it is assured that there is never an open unobstructed pathway between the reservoir and the fluid outlet. Also, by assuring that the pump only draws fluid from the reservoir when the pathway to the outlet is sealed off, it is also assured that a precise amount of fluid is moved with each pump cycle. This operation is completely timed by the linkage just described and occurs quickly, appearing to the patient that both actuator buttons are moving at the same rate.

When the extensions 250 and 252 of the pump button clear the abutment 262, they become locked in a snap action. This provides positive feedback to the patient that a dosage of medicament was delivered as desired. It also causes a full dose to be delivered. By virtue of the snap action of the pump actuator, only full doses may be administered.

When the medicament has been delivered, the spring loading of the actuator buttons returns the buttons to their first or initial position. During this time, the same timing provided by the block 154 is used for recharging the pump. More specifically, ramp 158 unlatches the ends of extensions 250 and 252 by lifting rod member 254. While the extensions 250 and 252 are being lifted by the ramp 158, the valve control button 116 is returning to the left to cause the outlet to be disconnected from the pump before the reservoir is reconnected to the pump for charging, thus sealing the outlet from both the pump and the reservoir before the reservoir is connected to the pump for recharging. This assures that the pump does not pull medicament from the patient but only from the reservoir. As the pump returns, a full dose of the medicament is drawn up into the piston chamber 170 to ready the device for the next dosage delivery.

Figure 7:
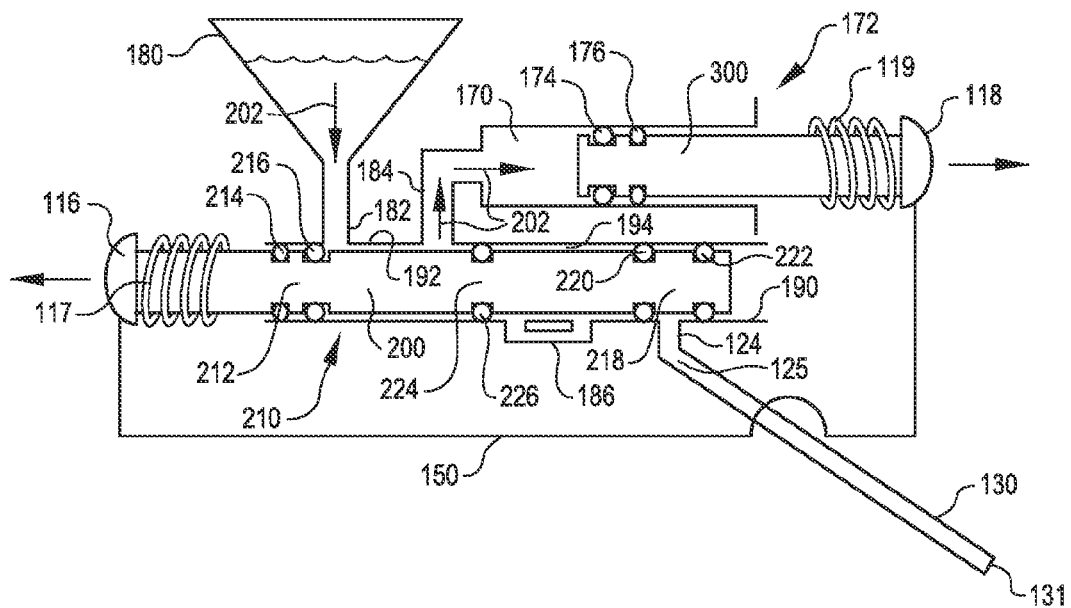
FIG. 7 is a schematic representation of the valves and pump of the device of FIG. 1 between medicament dosage deliveries and during the filling of the pump with the medicament.
Figure 8:
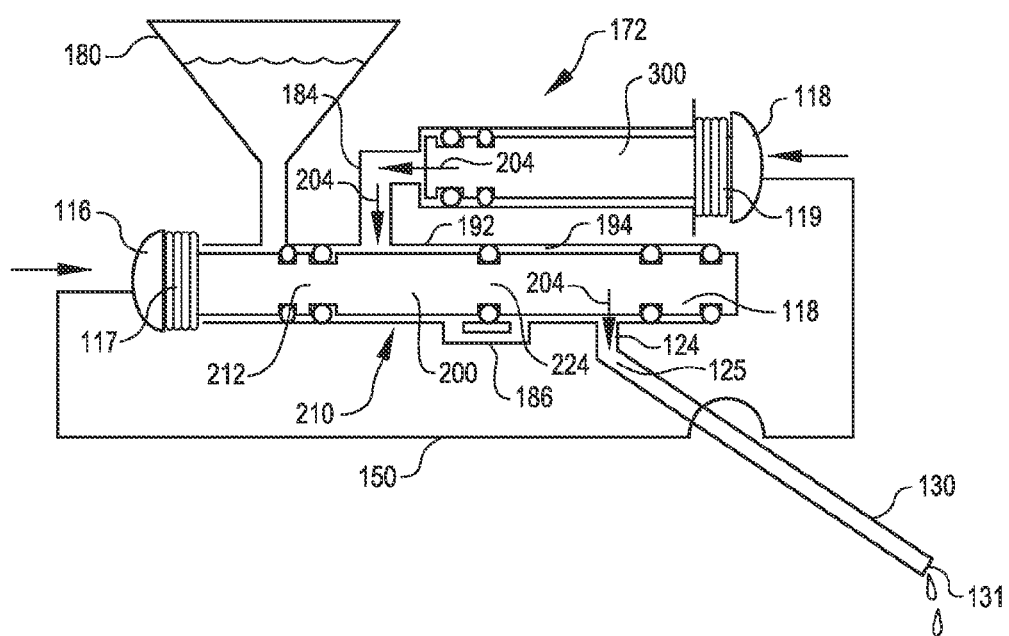
FIG. 8 is another schematic representation of the valves and pump of the device of FIG. 1 during medicament dosage delivery.

Referring now to FIGS. 7 and 8, they are schematic representations of the valves and pump of the device of FIG. 1 between medicament dosage filling (FIG. 7) and medicament dosage delivery (FIG. 8) As may be seen in FIGS. 7 and 8, the device 110 further includes a reservoir 222, a pump 224, and the cannula 130. The reservoir 222 may be formed as shown in FIG. 3 by the combination of the device base 160 and the flexible membrane 162. The device further includes the shuttle valve 210 including shuttle bar 200. The shuttle bar 200 is shown within the valve chamber 190. The shuttle bar 200 and O-rings 214 and 216 form a first valve 212, shuttle bar 200 and O-rings 220 and 222 form a second valve 234 and shuttle bar 200, O-ring 226 and a bypass channel 186 form a third valve 224. Although O-rings are used herein to form seals, other types of valve construction may employ forms of seals other than O-rings without departing from the invention.

The pump piston 300 is within the piston camber 170 to form a piston pump 172. The actuator control button 218 is directly coupled to and is an extension of the pump piston 226. It may also be noted that the actuator buttons 116 and 118 are spring loaded by springs 117 and 119, respectively. The springs are provided for returning the actuator buttons to a first or start position after a dosage is administered.

A fluid conduit 182 extends between the reservoir 180 and the valve 212. An annular conduit 192 extends between the O-rings 216 and 226, and an annular conduit 194 extends between the O-rings 226 and 220. A fluid conduit 184 provides a fluid connection between the reservoir 180 and the annular conduits 192 and 194 depending upon the position of the shuttle valve 210. Also illustrated in FIG. 7 is the linkage 150 that assures that the shuttle valve 210 is actuated before the piston pump 172 is actuated to provide a dose of medicament.

In FIG. 7, the valves are shown in a first configuration immediately after having returned to their first position following a dosage delivery. After the return of the valves, the linkage 150 permits the pump actuator 118 and piston 300 to return for refilling the pump chamber 300 in ready for the next medicament dosage delivery. During their return, the medicament flows as indicated by arrows 202 from the reservoir 180, through the conduit 182, through the annular channel 192, through conduit 184, and into the pump chamber 170.

As may be noted, when in the first position, the valves 218 and 224 isolate the outlet 124 from both the reservoir 180 and the piston pump 118. Having two such valves isolate the outlet 124 when the valves are in the first configuration provides an added degree of safety from medicament being inadvertently delivered to the patient between dosage deliveries. For example, this provides additional safety that the liquid medicament is not accidentally administered to the patient notwithstanding the inadvertent application of pressure to the reservoir. In applications such as this, it is not uncommon for the reservoir to be formed of flexible material. While this has its advantages, it does present the risk that the reservoir may be accidentally squeezed as it is worn. Because the valves 118 and 124 isolate the outlet 124 when the valves are in their first configuration, this redundant protection assures that pressure, accidentally applied to the reservoir, will not cause the fluid medicament to flow to the cannula.

In addition to the linkage 150 preventing return of the piston 300 until after the valves return to their first and start positions, the O-rings on the shuttle bar 200 are also spaced apart to insure that the valves 218 and 224 isolate the outlet 124 from the pump 172 and reservoir 180 before the pump is again connected to the reservoir. The O-ring spacing thus effectively forms a second linkage to assure that the cannula 130 is connected to the pump 172 only when a dosage is to be delivered and that it is never connected to the reservoir 180.

In operation, the pump chamber 170 is first filled as the actuator button 118 returns to the first position after having just delivered a medicament dosage. In this state, the shuttle valve 210 is set so that the first valve 212 will be open and the second and third valves 218 and 224 will be closed. This establishes a first fluid path indicated by arrows 202 from the reservoir 180 to the pump chamber 170 to fill the piston pump 172. When the patient wishes to receive another dose of medicament, the actuator buttons are concurrently pressed. The aforementioned linkages, including linkage 150, cause the first valve 212 to close and the second and third valves 218 and 224 to thereafter open. Meanwhile, actuation of the pump 172 is precluded until the first valve 212 is closed and the second and third valves 118 and 224 are opened. At this point a second fluid path indicated by arrows 204 is established from the pump chamber 170 to the cannula 130. The medicament is then administered to the patient through the distal end 131 of cannula 130.

Once the medication dosage is administered, the piston 330, and thus the actuator button 118, is returned under the spring pressure of spring 119 to its initial position. During the travel of the piston back to its first position, a given volume of the liquid medicament for the next dosage delivery is drawn from the reservoir into the pump chamber 170 as described above to ready the device for its next dosage delivery.

Referring now to FIG. 9, it is a sectional view in perspective showing the valve configuration of the device 110 of FIG. 1 during medicament filling of the pump chamber 170 immediately after a dosage delivery. Here, it may be clearly seen that the first actuator button 116 is directly coupled to the shuttle bar 200 of the valves 212, 218, and 224. Above the valves are the conduits from the reservoir, from the pump, and to the cannula. More particularly, the conduit 182 is in fluid communication with the reservoir, the conduit 184 is in fluid communication with the pump, and the conduit 124 is in fluid communication with the cannula. The valves are shown with the first valve 212 opened, communicating reservoir conduit 182 with the pump conduit 184 through channel 192, the second valve 218 closed and blocking the conduit 124 to the cannula, and the third valve 224 closed and blocking both the reservoir conduit 182 and the pump conduit 184 from the cannula conduit 124. This permits medicament to flow from the reservoir through conduit 182, through channel 192, and to the pump chamber 170 through conduit 184 as the actuator button 116 returns to its first position. Hence, the pump chamber is filled and ready for the next dosage delivery.

Referring now to FIG. 10, it is a sectional view in perspective similar to that of FIG. 9 but showing the valve configuration of the device 110 of FIG. 1 during medicament delivery. Here, the valves are shown with the first valve 212 closed and blocking the reservoir conduit 182, the second valve 218 opened permitting the outlet conduit 124 to communicate with the annular conduit 194, and the third valve 224 opened permitting medicament to flow from the annular conduit 192, through bypass 186, and to annular conduit 194. Thus, medicament is permitted to flow from the pump conduit 184, through annular conduit 192, through the bypass 186, through annular conduit 194, and into the outlet conduit 124 to administer the fixed volume dosage. As previously mentioned, the O-rings defining the first valve 212, the third valve 224, and the second valve 218 are spaced apart so that conduit 182 is blocked before conduits 184 and 124 are connected together through the valves 224 and 218.

FIG. 11 is a top perspective view of the base 160 of the device 110 of FIG. 1. Carried on the base 160 is the intermediate layer 164. Together, the base 160 and intermediate layer 164 define numerous fluid conduits within the device 110. One such fluid conduit is designated with reference character 270 in FIG. 11. The conduit 270 is within the fluid path that leads to the outlet 124. It is in the downstream portion of that path and takes a bend at 272 towards the bottom side of the base 160 where it, through an opening 274, enters a chamber 276 (FIG. 12). The chamber 276 communicates with the device outlet 124 that projects into the aforementioned cavity 120. When the cannula 130 (FIG. 13) is placed, it extends through an opening 123 in the cavity to beneath the patient's skin and communicates with the outlet 124 as described herein after.

The chamber 276 is partly defined by a seal rim 278 which receives a translucent cover 280 (FIG. 13). The top wall of the chamber 276 has an inverted cone shaped surface 282 portion and a tapered portion 284 to the outlet 124.

The translucent cover may be formed of transparent plastic wherein the surface that faces the chamber is roughed in a manner that renders the plastic cover translucent. The upper surface of the chamber is preferably coated with indicia which may, for example, be a color, such as blue. When the chamber is empty, the blue indicia will not be readily seen because the rough surface of the cover has rendered the cover translucent. However, when the chamber 276 is filled with a liquid, such as the liquid medicament, the cover 280 will become more transparent allowing the blue indicia to be readily seen. The chamber 276 and cover 280 thus form a prime indicator 286 adjacent the outlet 124. More particularly, the prime indicator 286 is immediately adjacent the outlet 124 since when the chamber is filled and the indicia readily seen, it will be known that the conduits and cannula are sufficiently prime with medicament to permit a full dosage to be delivered upon the next activation of the device 110.

In use, it is contemplated that the reservoir be filled through a fill port 290 on the bottom of the device 110 before the device is deployed on the patient's skin. After the device is filled, the translucent cover or window 280 may be viewed during device priming. During the priming process, the actuators 116 and 118 may be depressed a number of times until the blue indicia on the top surface portions 282 and 284 of the chamber are seen through the window 280. This provides an indication to the user that the chamber 276, and more importantly, the conduits are sufficiently primed and full with medicament to enable actual dosage delivery upon the next actuation of the device 110. Hence, a prime indicator 286 is provided immediately adjacent the outlet 124.

In FIG. 13A, it may be seen that the removable non-adhesive layer 292, in accordance with this embodiment, includes two portions, a first portion 293 and a second portion 294. Each of the first and second layer portions 293 and 294, respectively, includes a tab 298 and 297 respectively that extend beyond the margins of the device base. This permits the tabs 297 and 298 to be grasped for effortless removal of the removable non-adhesive layer portion 294 and 293. The layer portion 293 includes cutouts. The cutouts 295 and 296 extend through the pad 115 (FIG. 2) to provide access to the device fill port 290 and the prime indicator window 280. Hence, as described above, the device 110 may be filled and primed for use before the removable layer portions 293 and 294 are removed for adhering the device to a patient's skin.

FIGS. 14-16 are sectional views in perspective of an occlusion detector and lock-out 350 according to an embodiment of the device of FIG. 1. FIG. 14 shows the occlusion detector and lock-out 350 prior to an intended dosage delivery, FIG. 15 shows the occlusion detector and lock-out 350 during to an intended dosage delivery, and FIG. 16 shows the occlusion detector and lock-out 350 during occlusion detection and just prior to lock-out.

The occlusion detector and lock-out 350 serves to detect, during each dosage delivery, blockages between the shuttle valve and the distal end 131 of the cannula 130 (FIG. 8). Such blockages are most likely to occur within the cannula and may result in an improper amount of medicament being delivered during an attempted dosage delivery. For example, the user might have an erroneous belief that a full dosage had been delivered when, in fact, a dosage of insufficient quantity had been delivered. As will be seen subsequently, the occlusion detector is responsive to pressure within the pathway from the shuttle valve to the outlet and cannula that occurs during an attempted dosage delivery when a blockage exists.

The occlusion detector 350 has an inlet 132 that communicates with the outlet 124 (FIG. 10) of the shuttle valve 210 and an outlet 134 that communicates with the prime indicator 286 (FIG. 12). Between the inlet 132 and the outlet 134 is a channel 136. Hence, the channel 136 is within the fluid path from the valve to the outlet 125 of the device that may be coupled to the cannula 130 (FIGS. 7 and 8). The occlusion detector 350 also includes a resilient diaphragm 352 over which the channel 136 extends. Adjacent the diaphragm 352 is a deflectable stop 354. As will be seen subsequently, when there is an occlusion within the fluid path, an attempted dosage delivery results in an increased back pressure against the diaphragm 352 and the deflectable stop 354. This causes the deflectable stop 354 to engage a projection 157 of the linkage 150. This disables the linkage 150 that controls the interaction of the actuator buttons 116 and 118 and that causes the actuator buttons 116 and 118 to become locked.

More particularly, as may be further seen in FIG. 14, the linkage 150 is adjacent the occlusion detector 350. When the actuator buttons are depressed, the projection 157, carried by the extension 152 of the valve actuator button 116, slides across block 255 carried on pivot 256.

As may be seen in FIG. 15, upon further depression of buttons 116 and 118, the projection 157 slides past the distal end of the deflectable stop 354. It may also be seen that, as previously described, the rod member 254 has ridden up the first ramp 156 and down the second ramp 158 of block 154. This causes the first ramp 156 to engage a ramp surface 257 of block 255.

If no occlusion exists within the fluid path to the cannula, the blocks 154 and 255 and the actuator buttons 116 and 118 will return as previously described under spring pressure. However, if an occlusion does exist within the fluid path to the cannula, back pressure will quickly build in the channel 136 to cause the deflectable stop 354 to be deflected downwardly. This is shown in FIG. 16. The deflectable member 354 is now aligned with the projection 157. When, under spring pressure, the actuator buttons 116 and 118 are urged to their starting positions, the projection 157 will be caught by the deflectable stop 354 to lock the device and preclude its further use. Still further, the deflectable stop 354 or the projection 157 may be breakable or permanently deformable upon their engagement. This would render the linkage 150 jammed and irreversibly locked to permanently preclude further use of the device.

Figure 17:
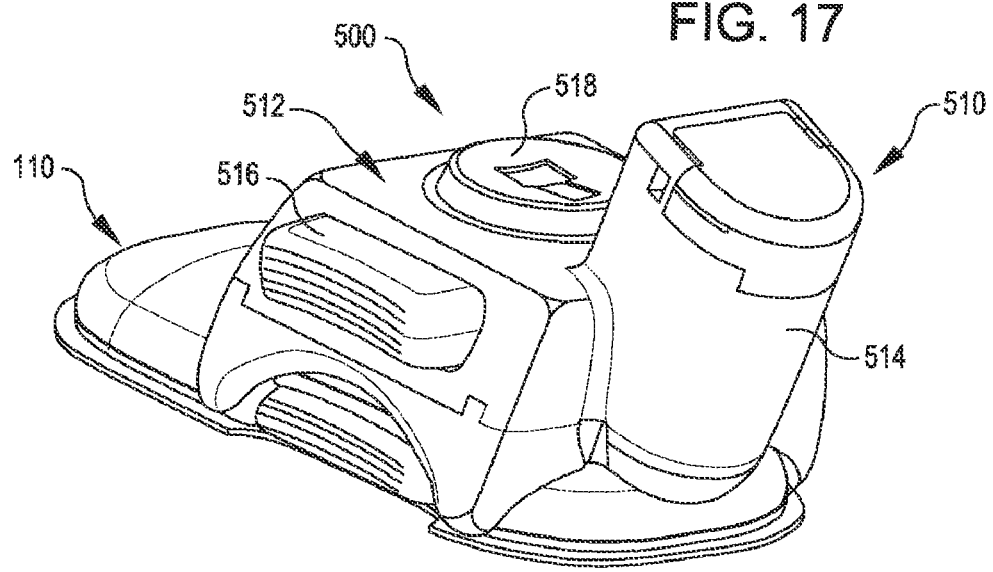
FIG. 17 is a perspective view of the device of FIG. 1 and a cannula placement assembly attached thereto ready to provide the device with a cannula according to a still another embodiment.

Referring now to FIG. 17, it is a perspective view of the device 110 of FIG. 1 with a cannula placement assembly 500 releasably attached thereto ready to provide the device with a cannula according to a still another embodiment. It is contemplated that the device 110 and cannula placement assembly 500 be pre-attached to each other upon delivery to a patient and that upon placement of the cannula, the cannula placement assembly 500 be automatically separated from the device 110.

The cannula placement assembly 500 generally includes a cannula driver portion 510 and an actuation portion 512. The cannula driver portion 510 is generally cylindrical in shape including a drive cylinder 514. The actuation portion includes an actuator button 516 and a safety control button 518. As will be seen subsequently, the safety control button 518 must first be depressed into a locked depressed position before the actuator button 516 may be depressed to set the cannula placement sequence into motion.

Figure 18:
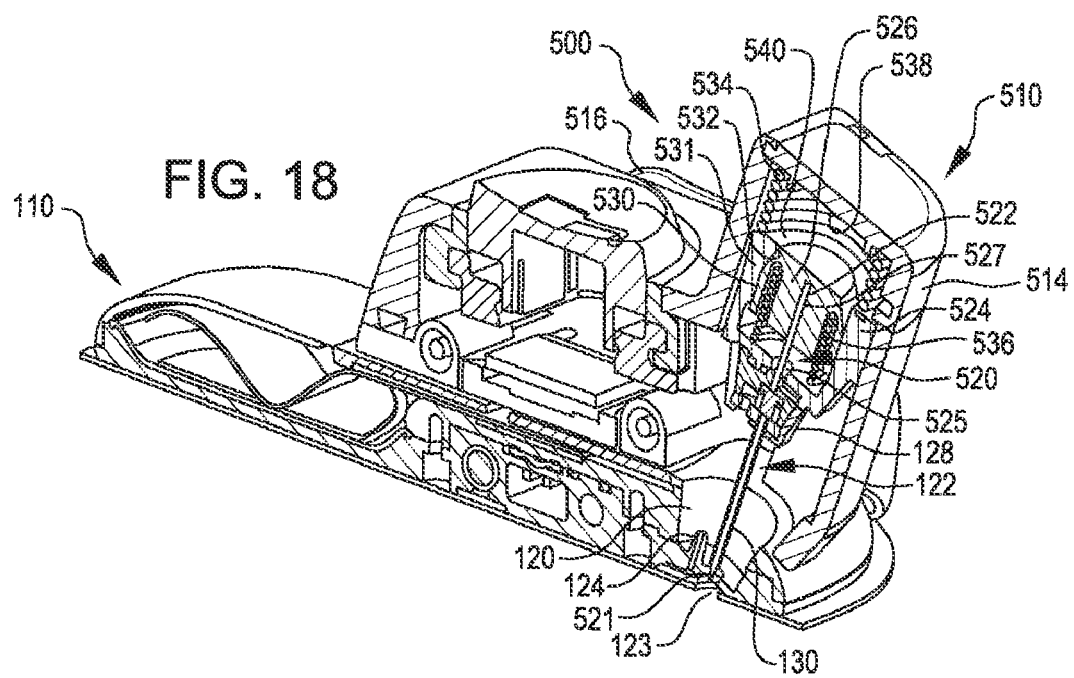
FIG. 18 is a sectional view, in perspective, to an enlarged scale, of the device and cannula placement assembly before the cannula is deployed.

FIG. 18 is a sectional view, in perspective, to an enlarged scale, of the device 110 and cannula placement assembly 500 before the cannula is deployed. As may be noted in FIG. 18, the interior components of the cannula driver portion 510 includes a plunger 524, a needle assembly 520, and the cannula assembly 122.

The cannula assembly, as previously described, includes the cannula 130, of the type known in the art, and a cannula carrier 128. The cannula carrier 128 is arranged to be received within the cavity 120 into which the device outlet 124 projects. Once the cannula carrier 128 is received into the cavity 120, the cannula carrier 128 establishes a fluid path from the outlet 124 to the cannula 130.

The needle assembly 520 includes a drive needle 522. The drive needle 522 includes a needle head assembly 526 and a needle shaft 527. Before the cannula 130 is placed, the cannula assembly 122 is carried by the needle assembly 520 and more specifically, by the cannula 130 being received on the drive needle 522 with the cannula carrier 128 being immediately adjacent the drive plunger 524 as shown.

The needle head assembly 526 is initially seated within the drive plunger 524. To that end, the needle head assembly 526 is within the plunger 524 and has an exterior surface 530 that conforms to the interior surface 532 of a wall portion 531 of the plunger 524. The needle shaft 527 extends from the needle head assembly 526, through an opening of the plunger 524, through the cannula carrier 128, and finally through the cannula 130 to terminate at a tip 521. During cannula placement, the cannula 130 and drive needle 522 extend through the opening 123 of the device 110.

The cannula driver 510 further includes a first drive spring 534 and a second drive spring 536. The first drive spring is originally compressed between an inner end wall 538 of the drive cylinder 514 and a top surface 540 of the plunger 524. The first drive spring 534 serves to drive the plunger 524 downwardly to in turn drive the cannula 130 and the drive needle 522 through the opening 123.

The plunger 524 is released by the actuator button 516 being depressed. As will be seen subsequently, the actuator button 516 includes a portion that interferes with a shoulder of the plunger 524. When the actuator button is depressed, that interference is resolved and the drive carrier 524 is free to move downwardly under the influence of the first drive spring 534. The needle tip 521 pierces the patient's skin and the lower portion of the needle shaft 527 and cannula 130 are placed beneath the patient's skin. The cannula 130 and needle 522 quickly reach the fully driven, temporary, configuration shown in FIG. 19.

In FIG. 19, it may be seen that the cannula 130 and needle shaft 527 upon which the cannula 130 is carried have been driven through the opening 123 of the device 110. The first drive spring 534 is now in an extended condition.

When the cannula driver 510 reaches the configuration shown in FIG. 19, the wall portion 531 of the plunger 524 clears a shoulder 542 of a short wall portion 544 of the drive cylinder 514. The wall portion 531 springs outwardly separating the conformal surfaces 530 and 532 of the wall portion 531 and the needle head 526, respectively. This frees the needle head 526 from the plunger 524. The needle head 526 is now free to move upwardly out of and away from the plunger 524 under the influence of the second drive spring 536.

As the needle head 526 moves upwardly, it of course takes the needle shaft 527 with it. When the needle head 526 reaches the extent of its travel (FIG. 20) by the extension of the second drive spring 536 (the first drive spring 534 has been omitted from the figure for clarity), the needle shaft 527 is fully extracted from the cannula 130 leaving only the cannula 130 beneath the patient's skin. The cannula carrier 128 has also been received within the cavity 120 of the device 110. As the cannula carrier 128 is received within the cavity 120, the device outlet 124 is placed into fluid communication with the cannula 130 through the cannula carrier 128.

Figure 21:
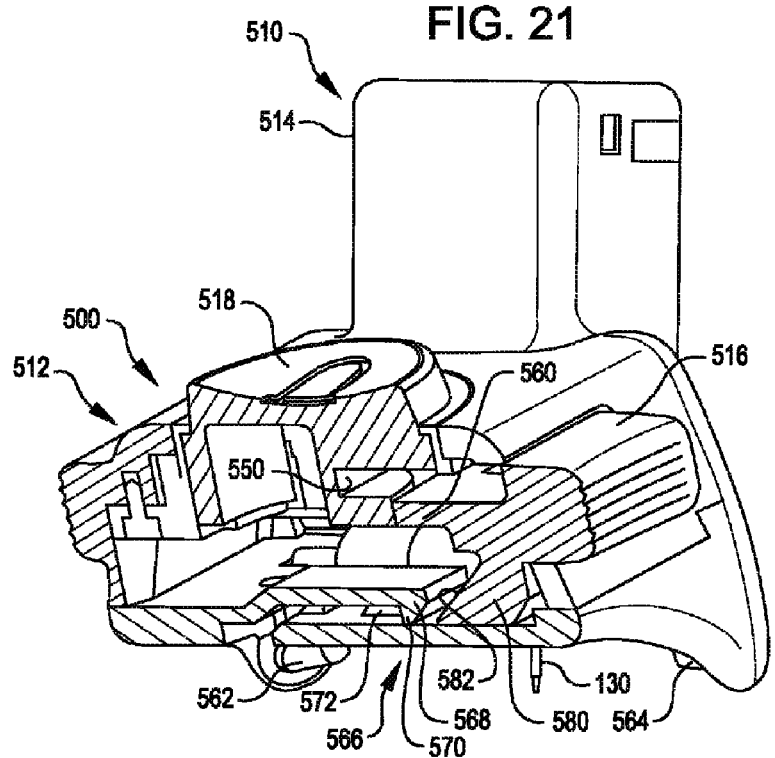
FIG. 21 is a sectional view, in perspective, of the cannula placement assembly of FIG. 17, showing the driver prior to cannula deployment.

FIG. 21 is a sectional view, in perspective, showing details of the actuator portion 512 of the cannula placement assembly 500 of FIG. 17, as configured prior to cannula deployment. As previously described, the actuator portion 512 includes the safety control button 518 and the actuator 516.

The safety control button includes a recess 550 and the actuator button 516 includes an extension 560. Before actuation, the extension 560 of the actuator 516 abuts the safety control button to preclude the depressing of the actuator 516. However, when the safety control button is depressed, as will be seen subsequently, the recess 550 is brought into alignment with the extension 560 to permit the actuator 516 to be depressed for setting into motion the placement of the cannula 130 as previously described.

As may also be noted in FIG. 21, the cannula placement assembly 500 further includes a plurality of projections 562 and 564. It is also contemplated that the cannula placement assembly 500 includes two additional such projections. The projections are arranged to be received within corresponding pockets of the wearable infusion device to permit the cannula placement assembly 500 to be releasably carried on the device 110 as shown, for example, in FIG. 17. For example, projection 562 is intended to be received by pocket 140 of the device 110 of FIGS. 1 and 2. The distance between the projections 562 and 564 is maintained by a latch 566 that includes a bendable arm 568 and a catch 572. The bendable arm includes a hook 570 at its distal end that is held by the catch 572. At least one urging member in the form of springs 573 and 575 (FIG. 20) serve to provide a continuous force for separating the projections 562 and 564. That force also maintains the hook 570 locked onto the catch 572, and the hook 570 being locked onto the catch 572 maintains the projections within their respective pockets to releasably maintain the cannula placement assembly 500 on the device 110.

The actuator 516 still further includes a latch release projection 580. The latch release projection 580 includes a ramped surface 582 arranged to engage and bend the bendable arm 568 as the actuator 516 is depressed. Eventually, sufficient depression of the actuator 516 bends the arm 568 sufficiently to cause the hook 570 to clear the catch 572. The actuator is shaped in such a manner that, as it is depressed in a single motion, it causes release and placement of the cannula before the hook 570 clears the catch 572. When the hook 570 clears the catch 572, the latch 566 is released and the projections, including projections 562 and 564 are forced apart under spring pressure to cause the cannula placement assembly 500 to be separated from the device 110.

Figure 22:
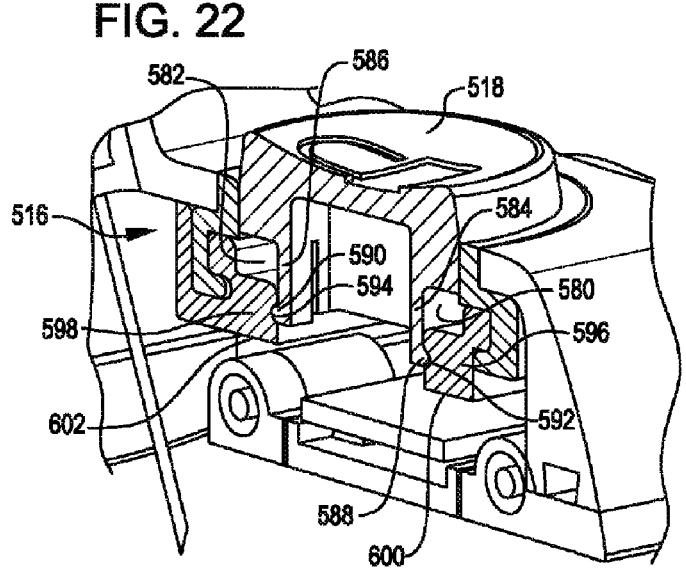
FIG. 22 is a sectional view, in perspective, and to an enlarged scale, of the cannula placement assembly of FIG. 17, showing the driver through a plane perpendicular to the sectional plane of FIG. 21 and prior to cannula deployment.

FIG. 22 is a sectional view, in perspective, and to an enlarged scale, of the cannula placement assembly of FIG. 17, showing the assembly through a plane perpendicular to the sectional plane of FIG. 21 and prior to cannula deployment. Here it may be seen that the control button 518 includes a pair of chordal recesses 580 and 582 that defined bendable legs 584 and 586 respectively. Each of the legs 584 and 586 includes a projecting foot 588 and 590 respectively. When the safety control button 518 is in a raised initial position as shown in FIG. 22, the foot 588 is confined within a slot 592 of an extension 598 of the actuator button 516 and the foot 590 is confined within a slot 594 of another extension 598 of the actuator button 516.

When the control button 518 is depressed, the legs 580 and 586 permit the feet 588 and 590 to slide out of their respective slots 592 and 594, respectively. They then progress downwardly until the legs 584 and 586 and feet 588 and 590 wrap about the extensions 596 and 598 of the actuator 516. The feet 588 and 590 become confined beneath bottom surfaces 600 and 602, respectively, of the actuator button extensions 596 and 598, respectively to lock the safety control 518 in the enable configuration of FIG. 23.

Figure 23:
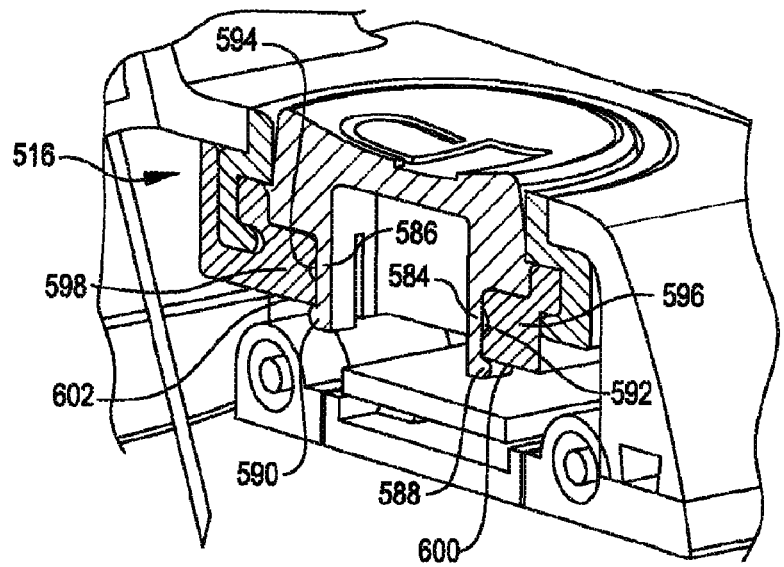
FIG. 23 is another sectional view similar to FIG. 22 showing the cannula placement assembly in an enabled configuration.

In FIG. 23 it may be clearly seen that the feet 588 and 590 are beneath and confined by the bottom surfaces 600 and 602, respectfully, of the actuator button extensions 596 and 598. The bendable legs 584 and 586 cause the control button 516 to enter this configuration with a snap action. This provides positive feedback to the user that the control button has been successfully depressed and that the cannula placement assembly is now ready for the depression of the actuator button 516. The confinement by the actuator extensions 596 and 598 of the feet 588 and 590 causes the control button 518 to be locked in the depressed enable state. This conveys to a user after use that the cannula placement assembly is not to be reused and even assists in making such reuse impossible or at least difficult.

With the control button now depressed and engaged in the enable configuration, the extension 560 of the actuator button 516 (FIG. 21) will now be aligned with the slot 550 of the control button 518. This permits the actuator to be depressed and actuated.

Figure 24:
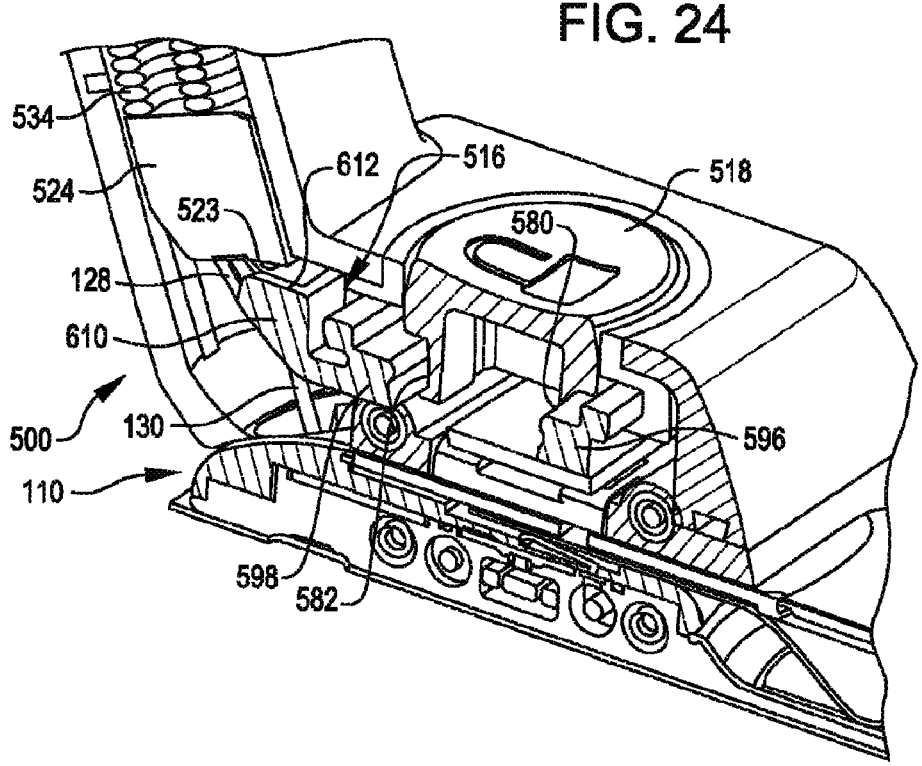
FIG. 24 is a sectional view, in perspective, and to an enlarged scale, showing the cannula placement assembly being released for deploying a cannula.
Figure 25:
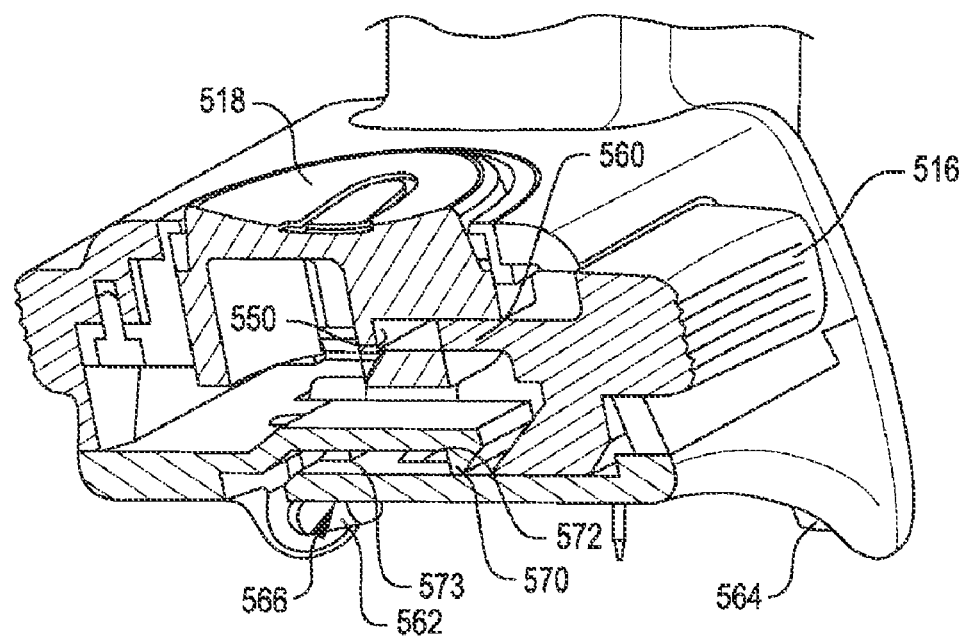
FIG. 25 is a sectional view, similar to that of FIG. 21, showing the cannula placement assembly during cannula deployment.

FIGS. 24 and 25 are sectional views showing the cannula placement assembly 500 as the actuator button 516 is being depressed. In FIG. 25 it may be seen that the extension 560 of the actuator button 516 is aligned with and entering into the slot 550 of the control button 518. As this occurs, the extension 598 slides in the chordal recess 582 of the control button 518 and the extension 596 slides in the chordal recess 580 of the control button.

The extension 598 further includes a wing 610 having an upper surface 612 that normally engages a lower surface 523 of the plunger 524 to interfere with the movement of the plunger 524 as previously described. As the actuator button 516 is depressed, the upper surface 612 of the extension 598 clears the lower surface 523 of the plunger 524. When this occurs, the drive carrier is released to be driven by spring 534 for placing the cannula 130 into a deployed position beneath the patient's skin.

FIG. 25 further shows that the latch 566 includes a second catch 573. The second catch 573 serves to catch the hook after it is lifted over the first catch 772. The second catch 573 is also positioned so that even though it catches the hook 570, the projections are still separated sufficiently to release the cannula placement assembly 500 from the device 110. The cannula placement assembly will not fall apart because it is held together in part by the second catch 572 catching the hook 570.

Figure 26:
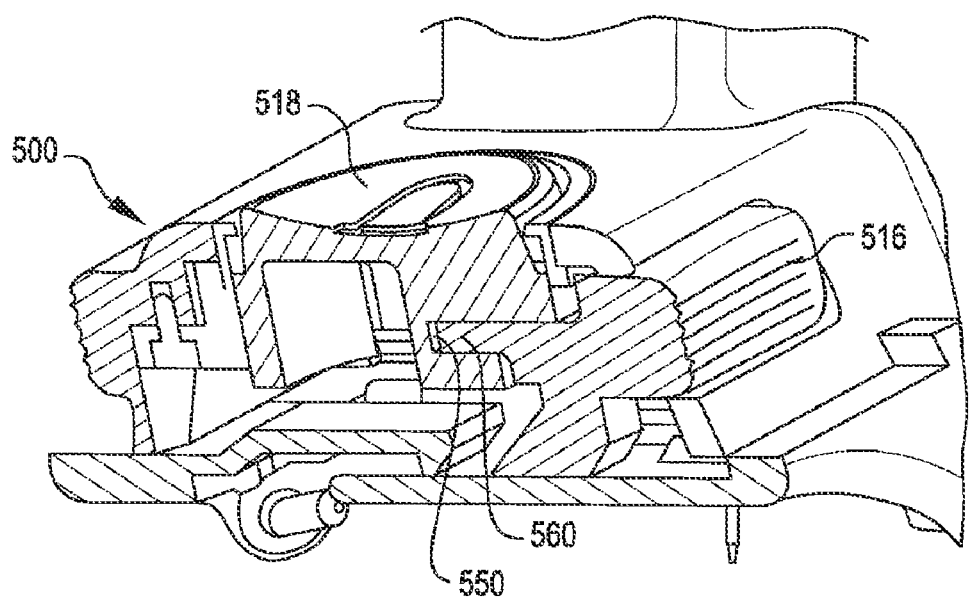
FIG. 26 is another sectional view, similar to that of FIG. 21, showing the cannula placement assembly after cannula deployment.

FIG. 26 is a sectional view showing the cannula placement assembly 500 after cannula deployment. The assembly is separated from the device. The projection 560 is fully within the slot 550 of the control button 518. This serves to further preclude reuse of the assembly 500 after cannula placement.

Figure 27:
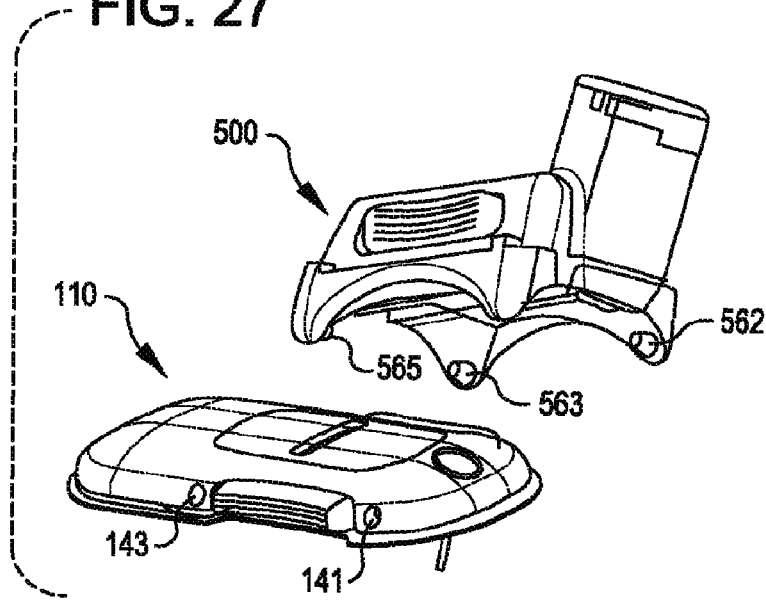
FIG. 27 is a perspective view of the device and cannula placement assembly after cannula deployment and separation of the cannula driver from the device.

FIG. 27 is a perspective view of the device 110 and cannula placement assembly 500 after cannula deployment and separation of the cannula placement assembly from the device. Clearly seen in FIG. 27 are the remaining projections 563 and 565 and remaining pockets 141 and 143 for releasably retaining the assembly 500 on the device 110. After cannula placement, the separated cannula placement assembly 500 may be discarded.

Figure 28:
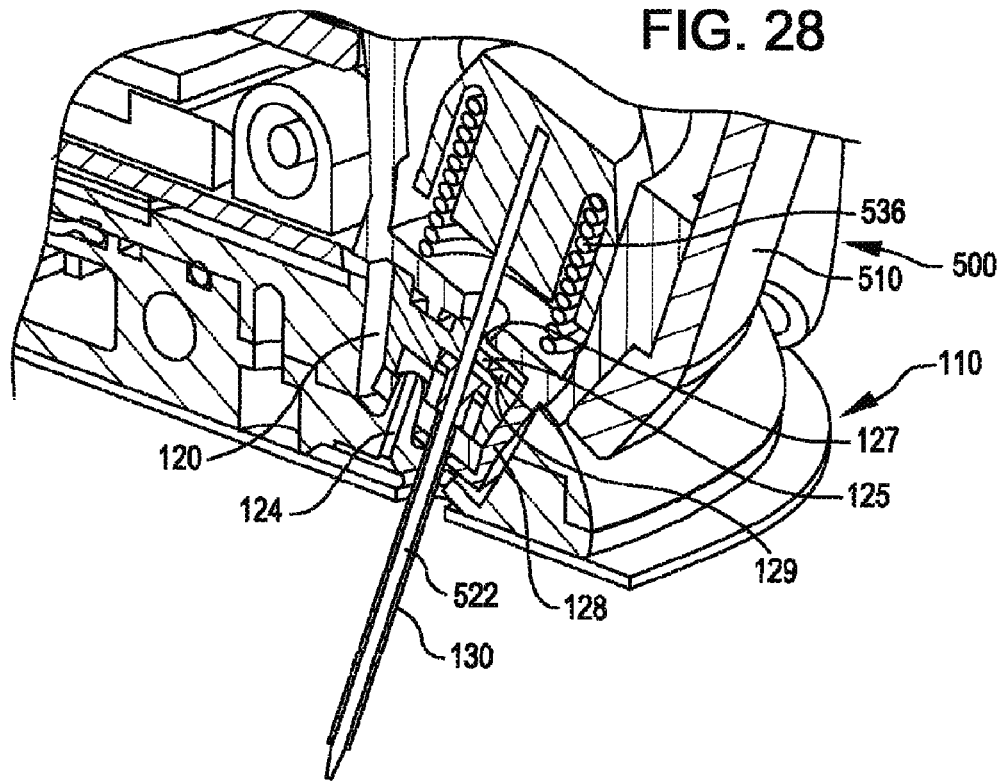
FIG. 28 is another sectional view of the cannula placement assembly and device to an enlarged scale showing the device and driver including details of a cannula needle port cover during cannula delivery.
Figure 29:
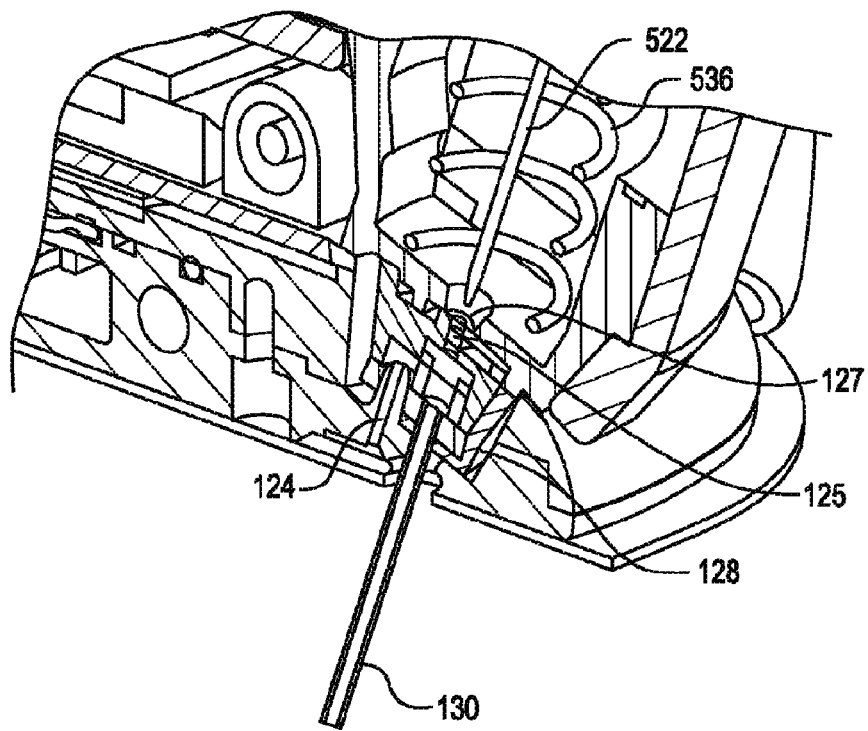
FIG. 29 is a sectional view similar to that of FIG. 28 showing the device and the cannula placement assembly including further details of the cannula needle port cover after cannula deployment.

FIG. 28 is a sectional view of the cannula placement assembly 500 and the device 110 to an enlarged scale showing details of a cannula needle port cover 125 during delivery of the cannula 130. The cannula 130 is carried on the cannula carrier 128. The cannula carrier includes a port 127 through which the needle 522 passes when it is retracted back into the driver 510 by the spring 536. To preclude access into the device and especially direct access to the cannula through the port 127 after the cannula 130 has been deployed, the cannula carrier 128 includes the port cover 125. In accordance with this embodiment, the port cover is made of relatively impenetrable material such as hard plastic or steel or the like and is substantially U-shaped and is confined within a slot 129. One leg of the port cover 125 is displaced and held away from the port 127 by the needle 522. It is a resilient material, such as spring steel and is held in place in, for example, a slightly compressed state, by the needle shaft 527 which is loaded through the hole in the port cover as shown at 125 in FIG. 28. Responsive to the cannula 130 being placed and the needle shaft 527 removed from the device 110, the one leg of the port cover is freed and permitted to spring to its natural shape such that the one leg overlies the port 127 as shown at 125 in FIG. 29 and in greater detail at 727 in FIG. 31. This results in the port 127 being blocked to preclude access to the interior of the device 110 once the cannula has been placed. Once the cannula 130 is deployed, the device 110 will appear as shown in FIG. 2. As previously mentioned, when the cannula 130 is placed, a fluid connection is established between the outlet 124 and the cannula 130 through the cannula carrier 128. After priming, the device 110 is ready to deliver its first dose of medicament.

Figure 30:
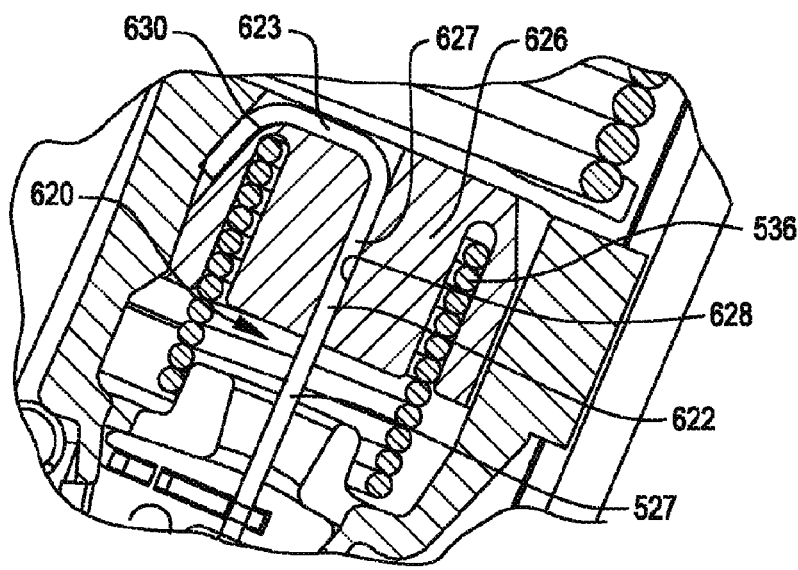
FIG. 30 is a sectional view, to an enlarged scale, showing a drive needle assembly including a drive needle and drive needle head according to a further embodiment of the invention.

FIG. 30 is a sectional view, to an enlarged scale, showing another driver needle assembly 620 including a drive needle shaft 622 and drive needle head 626 according to a further embodiment of the invention. Here it may be seen that the drive needle shaft 622 and the drive needle head 626 are two separate parts. The drive needle shaft 622 has a turned section 623 and an elongated section 627. The turned section 623 rides in a slot 630 of the drive needle head 626. The elongated section 627 passes through and is free to slide on a through bore 628 of the drive needle head 626. The needle assembly 620 may be used to assist in cannula placement and returned by spring 536 after cannula deployment in the same manner as previously described.

Figure 31:
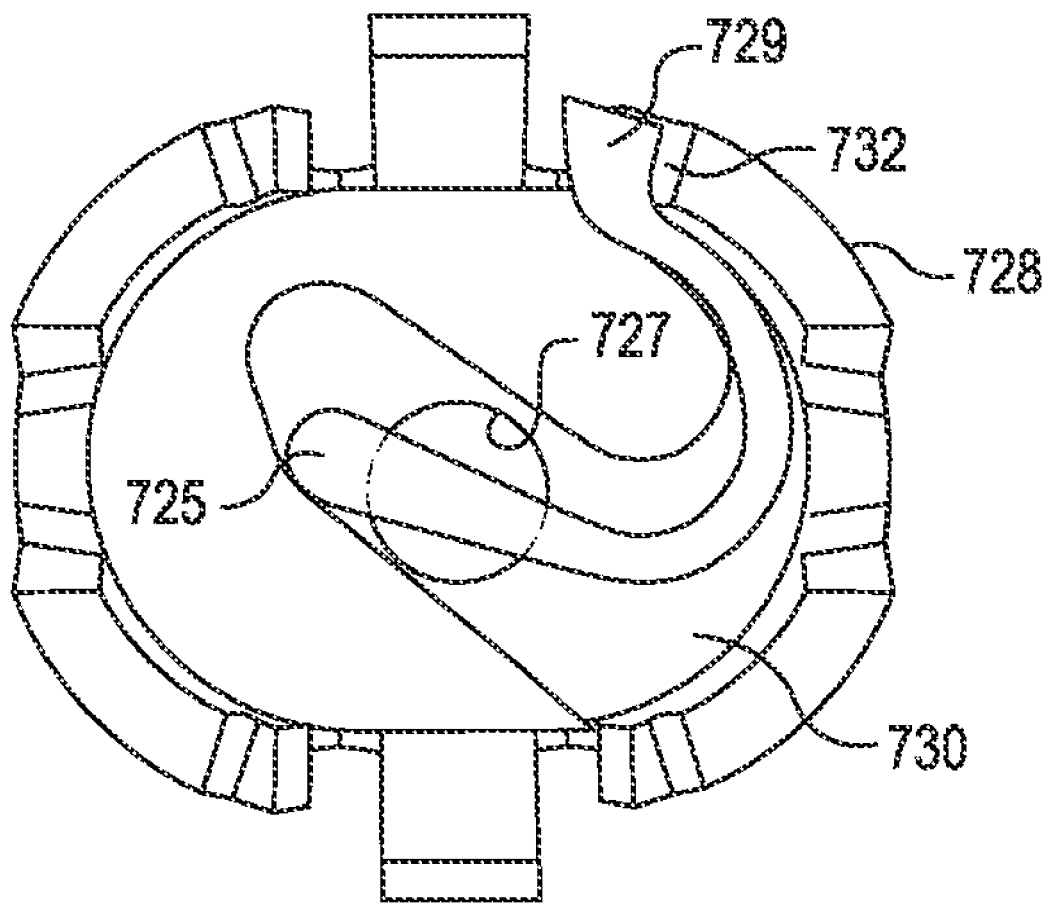
FIG. 31 is a sectional view, to an enlarged scale, illustrating an alternative embodiment of a cannula port cover after cannula deployment.

FIG. 31 is a sectional view, to an enlarged scale, illustrating an alternative embodiment of a cannula port cover 725. The port cover is shown covering a needle port 727 after cannula deployment. The port 727, as in the precious embodiment, is defined by the cannula carrier 728. The port cover 725 is generally U-shaped and confined in a cut-out 730. The cut-out 730 has a width that is greater than the diameter of the needle slot 727 to permit a cannula driver needle (not shown) to pass there through upon return after cannula placement. The port cover 725 has an end 729 that is confined by the cut-out 730 and a slot 732 formed in a side wall of the cannula carrier 728. The port cover 725 is therefore free to pivot to the position shown after the cannula driver needle (not shown) passes there through upon its return.

As may be noted in FIG. 31, the port cover 725 has a width, adjacent the port 727, that is smaller than the diameter of the port 727. While the port cover 725 does not completely cover the port 727, it is still of sufficient dimension to preclude access to the cannula through the port 727 by, for example, an external syringe needle.

While particular embodiments of the present invention have been shown and described, modifications may be made. It is therefore intended in the appended claims to cover all such changes and modifications which fall within the true spirit and scope of the invention as defined by those claims.

What is claimed is:

1. A wearable infusion device comprising:
   a base arranged to adhere to a person's skin for the wearing of the device outside of the person's body;
   a reservoir that holds a liquid medicament;
   an outlet port that delivers the liquid medicament to a patient;
   a pump that displaces a volume of the liquid medicament when actuated; and
   at least a first valve, a second valve, and a third valve, the valves establishing fluid connection between the reservoir and the pump when in a first valve configuration and establishing fluid connection between the pump and the outlet when in a second valve configuration, wherein at least two of the valves isolate the outlet from medicament flow from the reservoir when the valves are in the first valve configuration; and
   a manual control that opens and closes the valves to place the valves into the first and second valve configurations.

2. The device of claim 1, wherein the valves are arranged to prevent the outlet from being in fluid connection with the reservoir.

* * * * *